United States Patent
Buller et al.

(10) Patent No.: US 12,426,839 B2
(45) Date of Patent: Sep. 30, 2025

(54) METHOD FOR ESTIMATING CORE BODY TEMPERATURE

(71) Applicant: The Government of the United States, as Represented by the Secretary of the Army, Fort Detrick, MD (US)

(72) Inventors: Mark Jonathan Buller, Douglas, MA (US); David Patrick Looney, Framingham, MA (US)

(73) Assignee: The Government of the United States, as represented by the Secretary of the Army, Ft. Detrick, MD (US)

(*) Notice: Subject to any disclaimer, the term of this patent is extended or adjusted under 35 U.S.C. 154(b) by 728 days.

(21) Appl. No.: 17/428,525

(22) PCT Filed: Feb. 7, 2020

(86) PCT No.: PCT/US2020/017136
§ 371 (c)(1),
(2) Date: Aug. 4, 2021

(87) PCT Pub. No.: WO2020/180454
PCT Pub. Date: Sep. 10, 2020

(65) Prior Publication Data
US 2022/0125388 A1    Apr. 28, 2022

Related U.S. Application Data

(60) Provisional application No. 62/802,373, filed on Feb. 7, 2019.

(51) Int. Cl.
*A61B 5/00*    (2006.01)
*A61B 5/0205*  (2006.01)
(Continued)

(52) U.S. Cl.
CPC .......... *A61B 5/7278* (2013.01); *A61B 5/0008* (2013.01); *A61B 5/02055* (2013.01);
(Continued)

(58) Field of Classification Search
CPC . A61B 5/7278; A61B 5/0008; A61B 5/02055; A61B 5/024; A61B 5/7225;
(Continued)

(56) References Cited

U.S. PATENT DOCUMENTS

| | | |
|---|---|---|
| 5,441,476 A | 8/1995 | Kitado et al. |
| 7,805,186 B2 | 9/2010 | Pulkkinen et al. |

(Continued)

FOREIGN PATENT DOCUMENTS

| | | |
|---|---|---|
| CA | 2650576 A1 | 10/2006 |
| FR | 2998158 A1 | 5/2014 |

(Continued)

OTHER PUBLICATIONS

International Search Report for International Application No. PCT/US20/17136 dated Aug. 26, 2020.
(Continued)

*Primary Examiner* — Sana Sahand
(74) *Attorney, Agent, or Firm* — Leigh Z. Callander

(57) ABSTRACT

The invention in at least one embodiment includes a method for determining the core body temperature of a person by determining an initial core body temperature and heart rate of said person; providing the initial core body temperature and heart rate of the person to a processor; and calculating a predicted core body temperature by the processor using an extended Kalman filter based on the heart rate and the initial core body temperature. In another embodiment, a system for performing the method.

20 Claims, 15 Drawing Sheets

(51) Int. Cl.
  A61B 5/024 (2006.01)
  G16H 10/60 (2018.01)
  G16H 50/30 (2018.01)
(52) U.S. Cl.
  CPC .......... *A61B 5/024* (2013.01); *A61B 5/7225* (2013.01); *A61B 5/7275* (2013.01); *A61B 5/742* (2013.01); *A61B 5/746* (2013.01); *G16H 10/60* (2018.01); *G16H 50/30* (2018.01)
(58) Field of Classification Search
  CPC ....... A61B 5/7275; A61B 5/742; A61B 5/746; A61B 5/725; A61B 5/0215; A61B 5/01; G16H 10/60; G16H 50/30
  See application file for complete search history.

(56) References Cited

U.S. PATENT DOCUMENTS

| | | | |
|---|---|---|---|
| 10,702,165 | B2 | 7/2020 | Buller |
| 2007/0239038 | A1 | 10/2007 | Nicolaescu et al. |
| 2008/0224866 | A1 | 9/2008 | Rehman |
| 2010/0280331 | A1 | 11/2010 | Kaufman et al. |
| 2011/0251495 | A1 | 10/2011 | Province et al. |
| 2012/0068848 | A1 | 3/2012 | Campbell et al. |
| 2012/0078127 | A1 | 3/2012 | McDonald et al. |
| 2014/0180027 | A1 | 6/2014 | Buller |
| 2015/0182130 | A1 | 7/2015 | Utter |
| 2017/0071477 | A1 | 3/2017 | Lin et al. |
| 2017/0150218 | A1* | 5/2017 | Oobuchi .............. H04N 21/442 |
| 2017/0238811 | A1* | 8/2017 | Buller .................. A61B 5/7278 |
| 2019/0029537 | A1 | 1/2019 | Buller |
| 2019/0192009 | A1 | 6/2019 | Reifman et al. |
| 2021/0113091 | A1 | 4/2021 | Reifman et al. |

FOREIGN PATENT DOCUMENTS

| | | |
|---|---|---|
| JP | 2005226902 A | 8/2005 |
| JP | 2009-142333 A | 7/2009 |
| WO | 2009034218 A1 | 3/2009 |
| WO | 2011032016 A1 | 3/2011 |
| WO | 2015185927 A1 | 12/2015 |
| WO | 2017181195 A1 | 10/2017 |
| WO | 2017181196 A1 | 10/2017 |
| WO | 2018039058 A1 | 3/2018 |

OTHER PUBLICATIONS

Moran et al., A physiological strain index to evaluate heat stress, American Journal oh Physiology, Jul. 1, 1998, pp. 129-134, vol. 275, Issue 1.

Frank et al., The cumulative heat strain index—a novel approach to assess the physiological strain induced by exercise heat stress, European Journal of Applied Physiology, Mar. 21, 2021, pp. 527-532, vol. 84, Issue 6.

Lim et al., Human thermoregulation and measurement of body temperature in exercise and clinical settings, Annals Academy of Medicine, Apr. 2008, pp. 347-353, vol. 37, No. 4.

Lee et al., Thermoregulation, pacing and fluid balance during mass participation distance running in a warm humid environment, European Journal of Applied Physiology, Mar. 17, 2010, pp. 887-898, vol. 109, Issue 5.

Byrne et al., The ingestible telemetric body core temperature sensor: a review of validity and exercise applications, British Journal of Sports Medicine, Dec. 16, 2006, pp. 126-133, vol. 41, Issue 3.

Wilkinson et al., The effect of cool water ingestion on gastrointestinal pill temperature, Medicine and Science in Sports Exercise, Mar. 2008, pp. 523-528, vol. 40, Issue 3.

Yamakage et al., Evaluation of newly developed monitor of deep body temperature, Journal of Anesthesia, Jul. 17, 2002, pp. 354-357, vol. 16, Issue 4.

Teunissen et al., Non-invasive continuous core temperature measurement by zero heat flux, Physiological Measurement, Mar. 28, 2001, pp. 559-570, vol. 32, Issue 5.

Gunga et al., A non-invasive device to continuously determine heat strain in humans, Journal of Thermal Biology, Jul. 2008, pp. 297-307, vol. 33, Issue 5.

Gunga et al., The Double Sensor—A non-invasive device to continuously monitor core temperature in humans on earth and in space, Respiratory Physiology & Neurobiology, Oct. 2009, pp. S63-S68, vol. 169, Supplement.

Havenith G., Individualized model of human thermoregulation for the simulation of heat stress response, Journal of Applied Physiology, May 2001, pp. 1943-1954, vol. 90, Issue 5.

Yokota et al., Thermoregulatory model to predict physiological status from ambient environment and heart rate, Computers in Biology and Medicine, Nov.-Dec. 2008, pp. 1187-1193, vol. 38, Issue 11-12.

Buller et al., Estimation of human core temperature from sequential heart rate observations, Physiological Measurement, Jul. 2013, pp. 781-798, vol. 34, Issue 7.

Niedermann et al., Prediction of human core body temperature using non-invasive measurement methods, International Journal of Biometeorology, Jun. 13, 2013, pp. 7-15, vol. 58, Issue 1.

Richmond et al., Prediction of core body temperature from multiple variables, Annals of Occupational Hygiene, Nov. 2015, pp. 1168-1178, vol. 59, Issue 9.

Potter et al., Mathematical prediction of core body temperature from environment, activity, and clothing: The heat strain decision aid (HSDA), Journal of Thermal Biology, Jan. 16, 2017, pp. 78-85, vol. 64.

Savvidis et al., Circadian rhythm disruption in cancer biology, Molecular Medicine, Dec. 2012, pp. 1249-1260, vol. 18, Issue 1.

Jagannath et al., Sleep and circadian rhythm disruption in neuropsychiatric illness, Current Opinion in Neurology, Apr. 23, 2013, pp. 888-894, vol. 23 Issue 5.

Shi et al., Circadian disruption leads to insulin resistance and obesity, Current Biology, Feb. 21, 2013, pp. 372-381, vol. 23, Issue 5.

Buller et al., Real-time core body temperature estimation from heart rate for first responders wearing different levels of personal protective equipment, Ergonomics, May 13, 2015, pp. 1830-1841, vol. 58, Issue 11.

Looney et al., Estimating Resting Core Temperature Using Heart Rate, Journal for the Measurement of Physical Behaviour, Jun. 2018, pp. 79-86, vol. 1, Issue 2.

U.S. Patent and Trademark Office, International Search Report, PCT Application No. PCT/US2017/047547, Oct. 25, 2017, pp. 1-2.

U.S. Patent and Trademark Office, Written Opinion of the International Searching Authority, PCT Application No. PCT/US2017/047547, Oct. 25, 2017, pp. 3-9.

Al-Mukhaizeem, F., et al., "Comparison of Temporal Artery, Rectal and Esophageal Core Temperature in Children: Results of Pilot Study", Pediatric Child Health, Sep. 2004, pp. 461-465, vol. 9, No. 9.

Baratchi, Mitra, et al., "Toward Decisive Garments for Heat Stress Risk Detection," ACM Digital Library, https://doi.org/10.1145/2968219.2972714, UbiComp/ISW'16 Adjunct, Sep. 12-16, 2016, pp. 1095-1100.

Belval, Luke N., "Thermoregulatory Responses of Runners following a Warm Road Race," University of Connecticut, UCONN Library, https://opencommons.uconn.edu/usp_projects/7, May 2, 2014, pp. 1-36.

Bland, J. and Altman, D., "Statistical methods for assessing agreement between two methods of clinical measurements," Lancet, 1986, pp. 307-310, vol. 1.

Brauer, A., et al., "Measurement of core body temperature during postoperative rewarming" (translated title), Der Anaesthesist, Fall 1997, pp. 683-688 (English abstract on p. 684), vol. 46.

Buller, M. J., et al., "Thermal Work Strain during Marine Rifle Squad Operations in Afghanistan (Mar. 2010)," USARIEM Technical Report No. T11-02 (AD A501301), Feb. 2011, pp. 1-39.

Buller, M.J., et al., "Estimation of Human Internal Temperature from Wearable Physiological Sensors," Proceedings of the Twenty-

(56) References Cited

OTHER PUBLICATIONS

Second Innovative Applications on Artificial Intelligence Conference (IAAI-10), 2010, pp. 1763-1768.
Buller, M.J. et al.; "Human Thermoregulatory System State Estimation Using Non-invasive Physiological Sensors", Engineering in Medicine and Biology Society, EMBC, 2011 Annual International Conference of the IEEE, Aug. 30 2011-Sep. 3 2011, pp. 3290-3293.
Buller, M.J., "Human Thermal-Work Strain Performance Optimization from wearable Physiological Sensors", Brown University, May 2015; pp. 23-73 and 159-162.
Bulut, Yalcin, et al., "Process and Measurement Noise Estimation for Kalman Filtering", Structural Dynamics, May 12, 2011, pp. 375-386, vol. 3.
Chen, Chi-Tsong, "Linear System Theory and Design", 3rd ed., Oxford University Press, 1999, pp. 106-111.
Cheuvront, Samuel et al., "Evaluation of the Limits to Accurate Sweat Loss Prediction During Prolonged Exercise", Eur. J. Appl. Physiol., 2007, pp. 215-224, vol. 101.
Cuddy, John S., et al., "A Reduced Core to Skin Temperature Gradient, Not a Critical Core Temperature, Affects Aerobic Capacity in the Heat", Journal of Thermal Biology, Jul. 2014, pp. 7-12, vol. 43.
Degroot, David W. et al., "Prediction Models for Core Temperature During Heat Stress Vary with Exercise Intensity," Medicine & Science in Sports & Exercise, May 2007, p. S436, vol. 39, issue 5.
Degroot, David W. et al., "Validation of the ICDA Model for Predicting Body Core Temperature," Medical & Science in Sports & Exercise, May 2008, p. S367, vol. 40, Issue 5.
Ely, Brett R., et al., "Evidence Against a 40° C. Core Temperature Threshold for Fatigue in Humans," Journal of Applied Physiology, Aug. 27, 2009, pp. 1519-1525, vol. 107, No. 5.
Esteve-Lanao, Jonathan, et al., "How Do Humans Control Physiological Strain during Strenuous Endurance Exercise?", PlusOne Journal, https://doi.org/10.1371/journal.pone.0002943, Aug. 13, 2008, pp. 1-11.
Fiala, Dusan, et al., "A Computer Model of Human Thermoregulation for a Wide Range of Environmental Conditions: The Passive System", Journal of Applied Physiology, Nov. 1, 1999, pp. 1957-1972, vol. 87, Issue 5.
Fiala, Dusan et al.,"Computer Prediction of Human Thermoregulatory and Temperature Responses to a Wide Range of Environmental Conditions", International Journal Biometeorol, 2001, pp. 143-159, vol. 45.
Fick, Adolph, "On liquid diffusion," Journal of Membrane Science, 1995, pp. 33-38, vol. 100.
Fox, R.H. et al., "A new method for monitoring deep body temperature from the skin surface," Clinical Science, 1973, pp. 81-86, vol. 44.
Gribok, Andrei, et al., "Regularization of Body Core Temperature Prediction during Physical Activity", Proceedings of the 28th IEEE EMBS Annual International Conference, New York, NY, Aug. 30-Sep. 3, 2006, pp. 459-463.
Grubbs, Frank E., "Procedures for detecting outlying observations in samples," National Technical Information Service, U.S. Department of Commerce, AD-781 499, BRL Report No. 1713, Apr. 1974, pp. 1-53.
Kalman, R.E., "A New Approach to Linear Filtering and Prediction Problems," Journal of Basic Engineering, Mar. 1960, pp. 35-45, vol. 82.
Karp, Jason R., "Heart Rate Training for Improved Running Performance," www.coachr.org/heart_rate_training_for_improvement.htm., printed on Mar. 29, 2016, pp. 1-6.
Kenefick, Robert W. et al., "DEET insect repellent: effects on thermoregulatory sweating and physiological strain," Eur. J. Appl. Physiol., 2011, pp. 3061-3068, vol. 111.
Kraning, Kenneth K., et al., "A mechanistic computer simulation of human work in heat that account for physical and physiological effects of clothing, aerobic fitness and progressive dehydration," Journal of Thermal Biology, 1997, pp. 331-342, vol. 22, No. 4/5.
Latzka, William A. et al., "Hyperhydration: thermoregualtory effects during compensable exercise heat stress," J. Appl. Physiol., 1997, pp. 860-866, vol. 83.
Latzka, William A. et al., "Hyperhydration: tolerance and cardiovascular effects during uncompensible exercise-heat stress," J. Appl. Physiol., 1998, vol. 84, pp. 1858-1864.
Laxminarayan, Srinivas, et al., "Individualized Estimation of Human Core Body Temperature Using Noninvasive Measurements", Journal of Applied Physiology, doi:10.1152/japplphysiol.00837.2017, Feb. 8, 2018, pp. 1387-1402, vol. 124.
Laxminarayan, Srinivas, et al., "Preventing Heat Injuries by Predicting Individualized Human Core Temperature", Proceedings of the HFM-254 Symposium on Health Surveillance and Informatics in Missions: Multidisciplinary Approaches and Perspectives, STO-MP-HFM-254, Oct. 12-14, 2015, pp. 21-1 to 21-11.
Lefrant, J.Y., et al., "Temperature measurement in intensive care patients: comparison of urinary bladder, besophageal, rectal, axillary, and inguinal methods versus pulmonary artery core method," Intensive Care Med., 2003, pp. 414-418, vol. 29.
Montain, Scott J., et al., "Influence of graded dehydration on hyperthermia and cardiovascular drift during exercise", Journal of Applied Physiology, 1992, pp. 1340-1350, vol. 73.
Oleng, Nicholas, et al., "Hybrid Approaches to Physiologic Modeling and Prediction", Proceedings of the Biomonitoring for Physiological and Cognitive Performance during Military Operations—International Society for Optical Engineering, Mar. 31-Apr. 1, 2005, pp. 193-203, vol. 5797.
Orderud, Fredrik, "Comparison of Kalman Filter Estimation Approaches for State Space Models with Nonlinear Measurements," In. Proc. of Scandinavian Conference on Simulation and Modeling, 2005, pp. 1-8.
Ozaki, Tohru, "The Local Linearization Filter with Application to Nonlinear System Identifications", Proceedings of the First US/Japan Conference on the Frontiers of Statistical, Modeling: An Informational Approach, 1994, pp. 217-240.
Pandolf, Kent B., et al., "Convergence of Skin and Rectal Temperatures as a Criterion for Heat Tolerance", Aviation, Space, and Environmental Medicine, Sep. 1978, pp. 1095-1101, vol. 49, No. 9.
Pokora, Ilona, et al., "Application of A Physiological Strain Index in Evaluating Responses to Exercise Stress—A Comparison Between Endurance and High Intensity Intermittent Trained Athletes," Journal of Human Kinetics, Mar. 2016, pp. 103-114, vol. 50.
Sargent II, Frederick et al., "Physiological Variability in Young Men", Physiological Measurements of Metabolic Functions, ed. CF Consolazio, RE Johnson and LJ Pecora, 1963, pp. 453-480, New York: McGraw-Hill.
Sawka, Michael N. et al., "Chapter 26 Physiological Systems and Their Responses to Conditions of Heat and Cold", ACSM's Advanced Exercise Physiology, ed. CM Tipton, MN Sawka, CA Tate, and RL Terjung, 2006, pp. 535-563, Williams & Wilkins, New York.
Seng, Kok-Yong, et al., "Nonlinear Mixed Effects Modelling for the Analysis of Longitudinal Body Core Temperature Data in Healthy Volunteers", Physiological Measurement, Mar. 10, 2016, pp. 485-502, vol. 37.
Steck, Luke N. et al., "Non-invasive Measurement of the Human Core temperature", International Journal of Heat and Mass Transfer, Jan. 2011, vol. 54, pp. 975-982.
Varela, Manuel, et al., "Holter Monitoring of Central and Peripheral Temperature: Possible Uses and Feasibility Study in Outpatient Settings", Journal of Clinical Monitoring and Computing, 2009, pp. 209-216, vol. 23.
Wan, Margaret, "Assessment of Occupational Heat Strain", Graduate Theses and Dissertations, University of South Florida, http://scholarcommons.usf.edu/etd/2745, 2006, pp. 1-17 and 27-43.
Welch, Greg et al., "An Introduction to the Kalman Filter", AMC, Inc., SIGGRAPH 2001, 2001, pp. 19-29, Course 8.
Wright-Beatty, Heather E. et al., "Increased Air Velocity During Exercise in the Heat Leads to Equal Reductions in Hydration Shifts and Interleukin-6 With Age", European Journal of Applied Physiology, Jun. 19, 2014, pp. 2081-2092, vol. 114, Issue 10.
English Abstract for FR2998158 A1, printed Mar. 21, 2016.
European Patent Office, extended European Search Report for Application No. 20766529.0, Jan. 9, 2022, pp. 1-11.

(56) References Cited

OTHER PUBLICATIONS

European Patent Office, Communication pursuant to Article 94(3) EPC for Application No. 20766529.0, Jul. 27, 2023, pp. 1-7.

U.S. Patent and Trademark Office, Non-Final Office Action in U.S. Appl. No. 16/767,970, Dec. 10, 2021, pp. 24-51.

European Patent Office, English abstract for JP2018134137A, printed on Apr. 28, 2023.

Looney, David P., et al., "Accuracy Of ECTemp Models In Predicting Core Temperature And Circadian Rhythm Indicators From Heart Rate": 1600 Board #275, American College of Sports Medicine, vol. 49, No. 5s, May 1, 2017, p. 454.

Pham, Sean, et al., "Wearable Sensor System to Monitor Physical Activity and the Physiological Effects of Heat Exposure," Sensors 2020, doi:10.3390/s20030855, Feb. 6, 2020, pp. 1-15.

Sawka, Michael N., et al., "Integrated Physiological Mechanisms of Exercise Performance, Adaptation, and Maladaptation to Heat Stress", Comprehensive Physiology, Oct. 2011, vol. 1, pp. 1883-1928.

English Abstract for JP2005226902 A, printed Mar. 21, 2016.

Cuddy, JS et al., "Skin Temperature and Heart Rate Can Be Used to Estimate Physiological Strain During Exercise in the Heat in a Cohort of Fit and Unfit Males", Military Medicine, Jul. 2013, pp. e841-e847, vol. 178.

\* cited by examiner

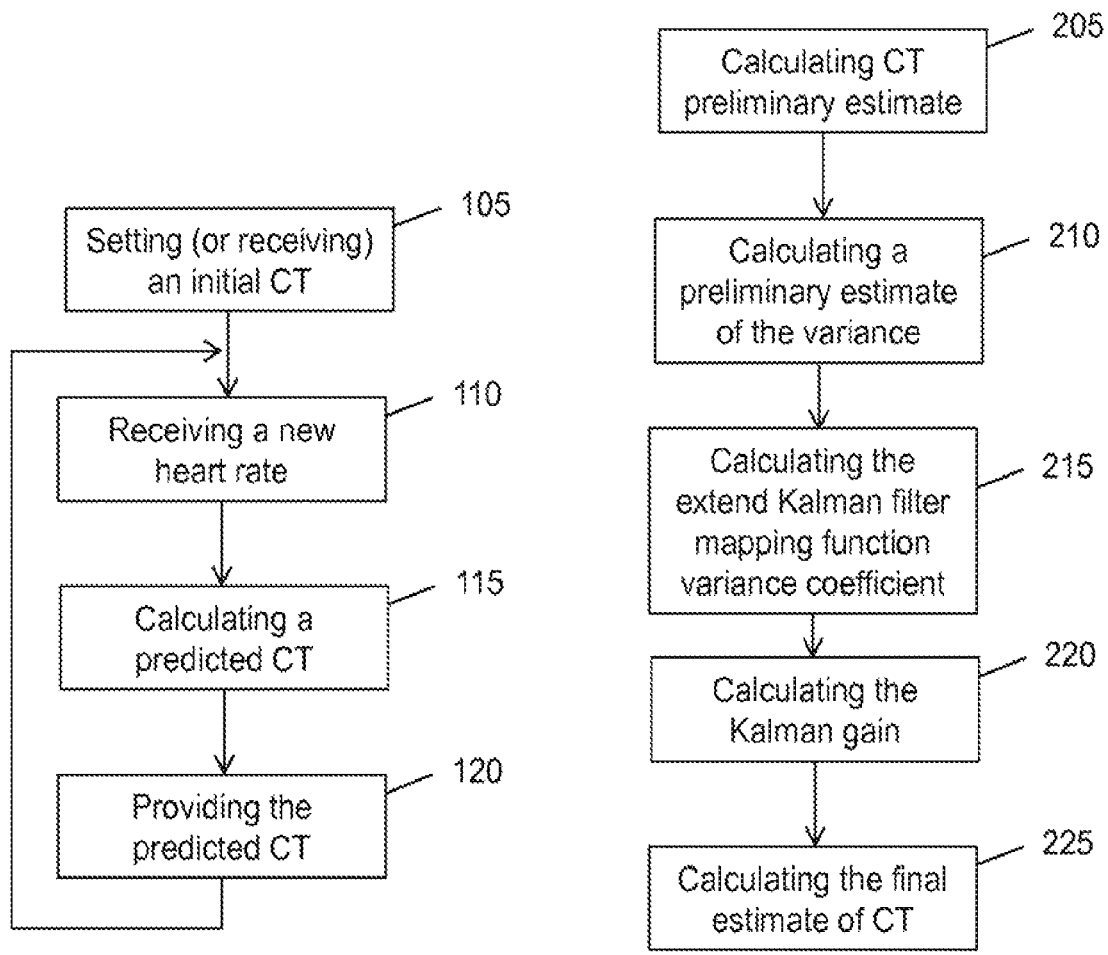
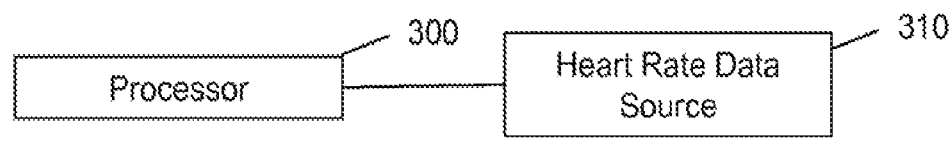

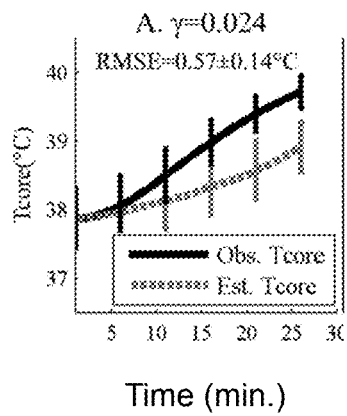
FIG. 4A1
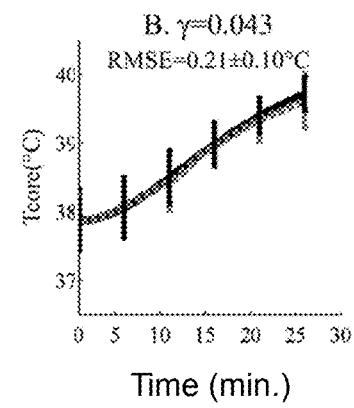
FIG. 4B1
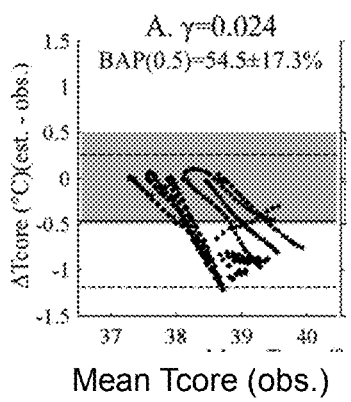
FIG. 4A2
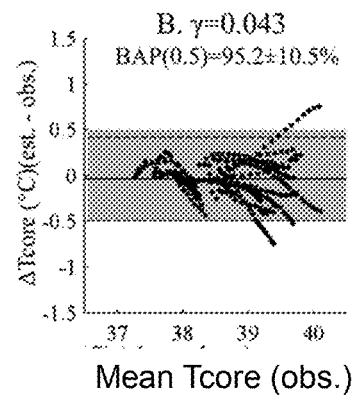
FIG. 4B2
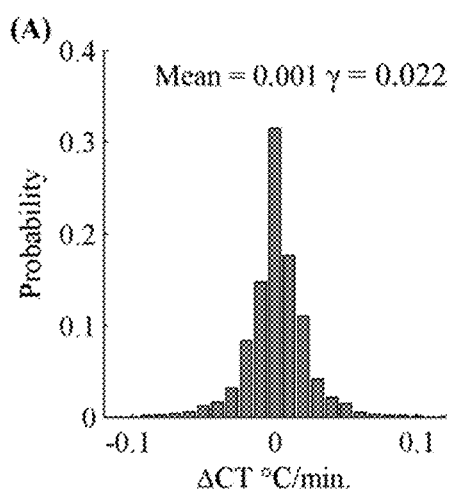
FIG. 5A
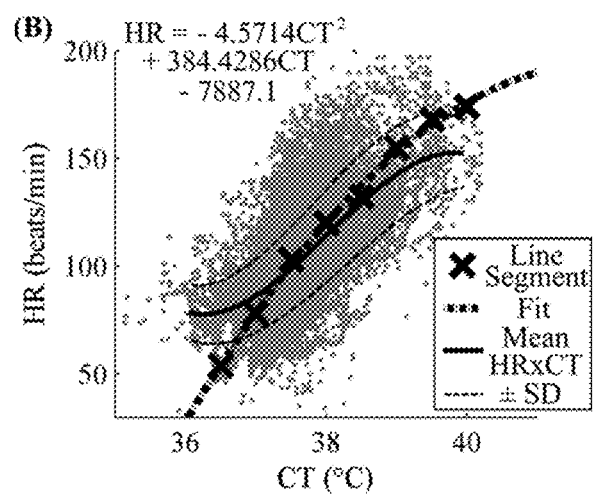
FIG. 5B

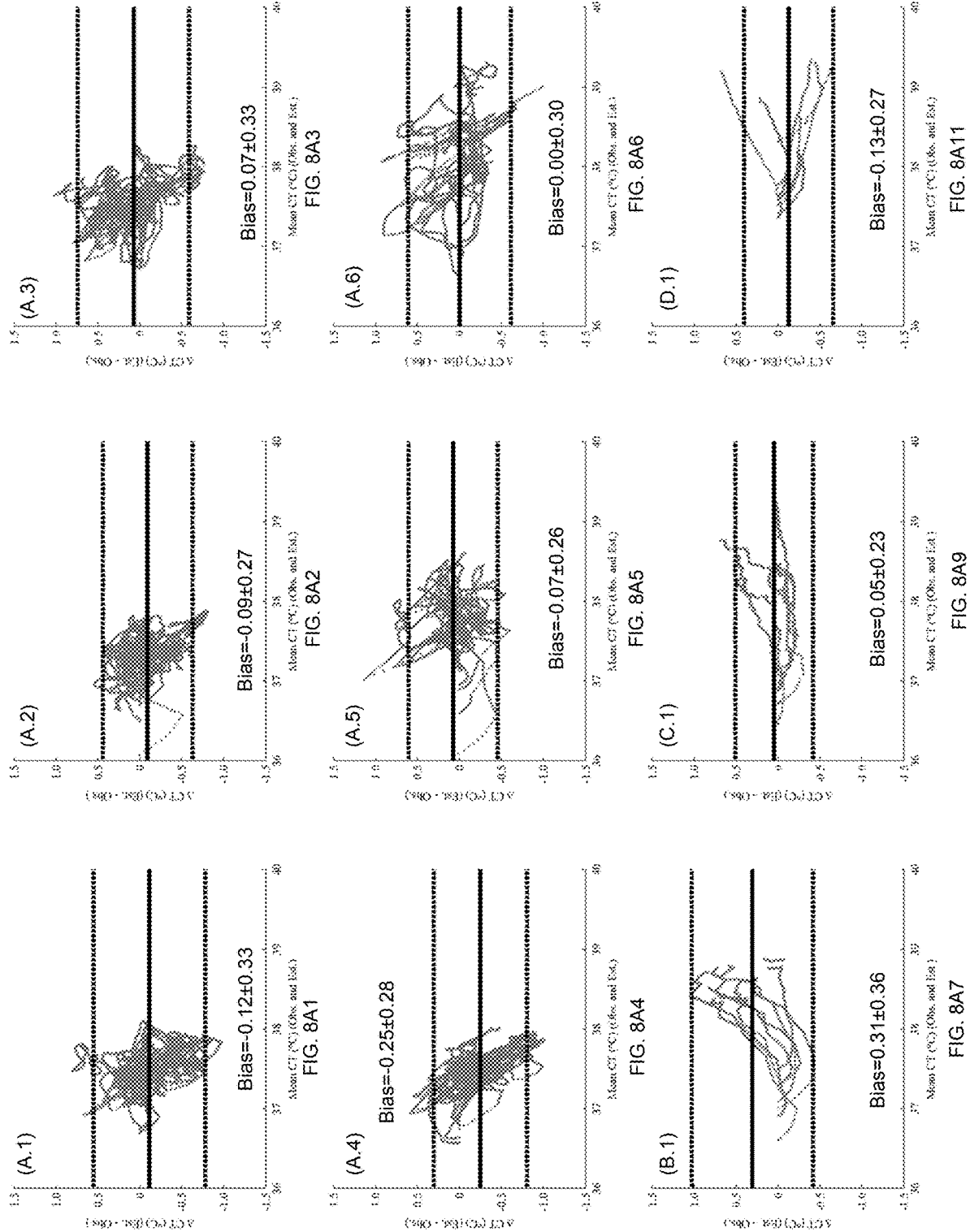
FIG. 8A1  FIG. 8A2  FIG. 8A3
FIG. 8A4  FIG. 8A5  FIG. 8A6
FIG. 8A7  FIG. 8A9  FIG. 8A11

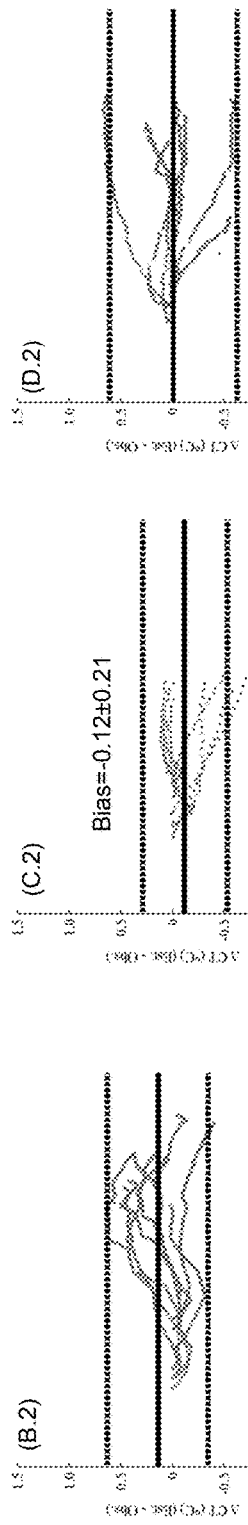
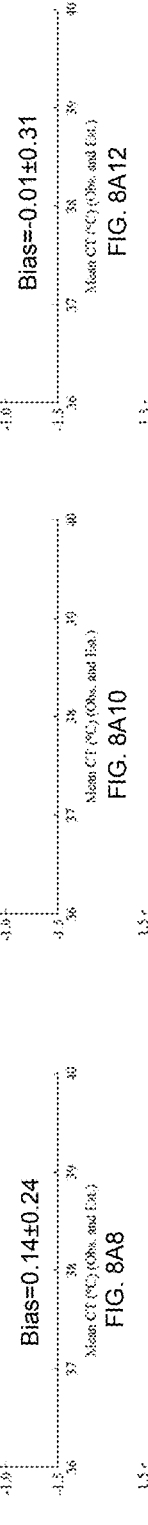
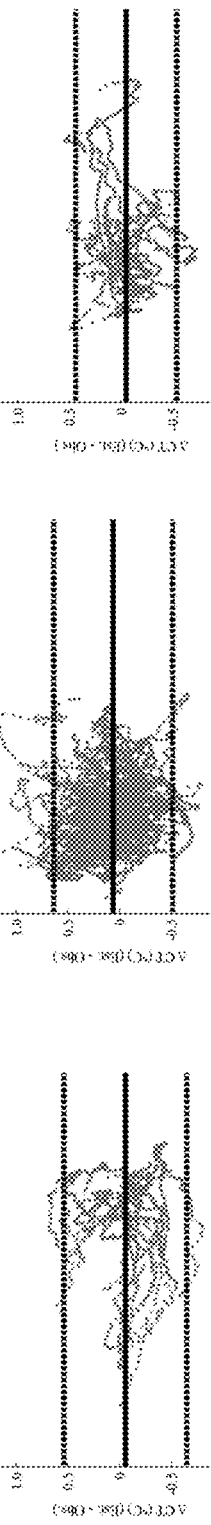
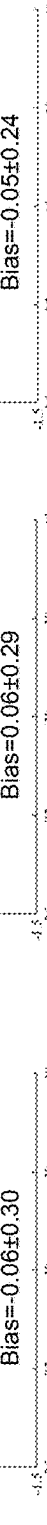
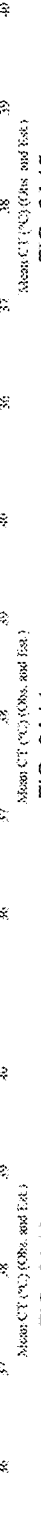
FIG. 8A8, FIG. 8A10, FIG. 8A12, FIG. 8A13, FIG. 8A14, FIG. 8A15, FIG. 8A16, FIG. 8A17, FIG. 8A18

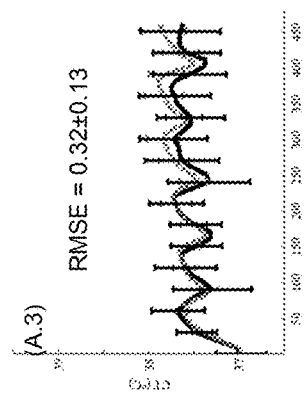
FIG. 8B1
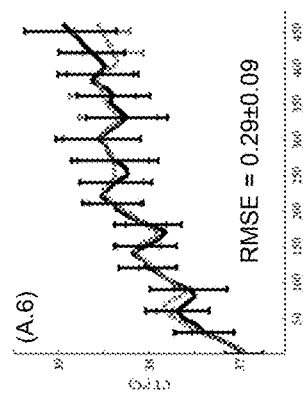
FIG. 8B2
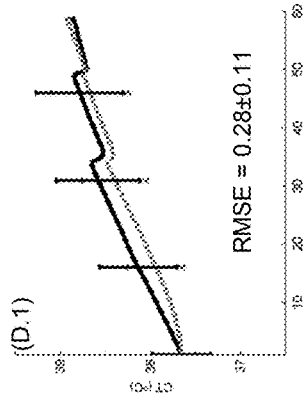
FIG. 8B3
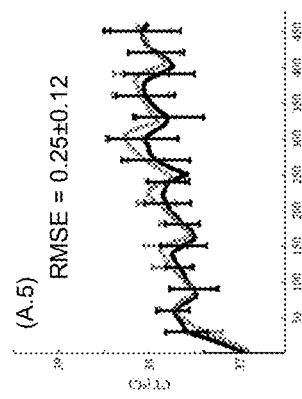
FIG. 8B5
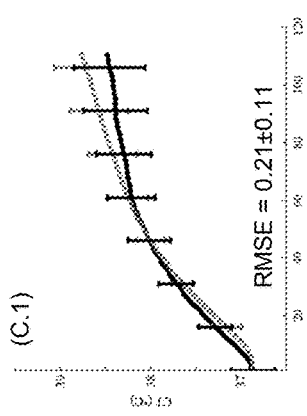
FIG. 8B6
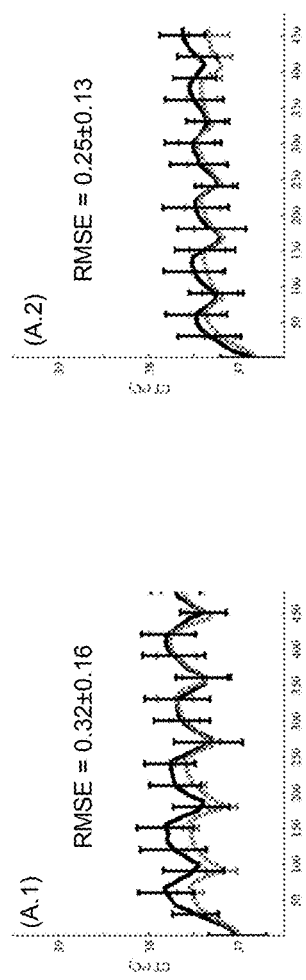
FIG. 8B4
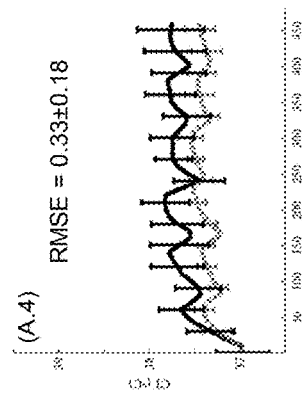
FIG. 8B9
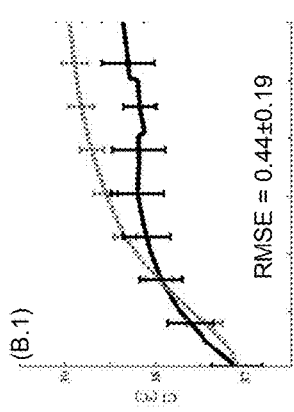
FIG. 8B11

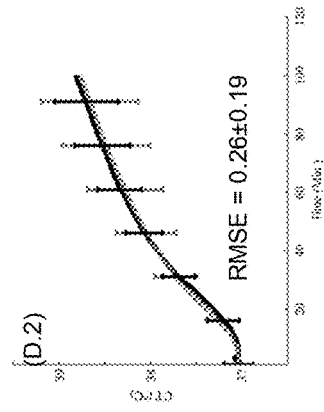
FIG. 8B10
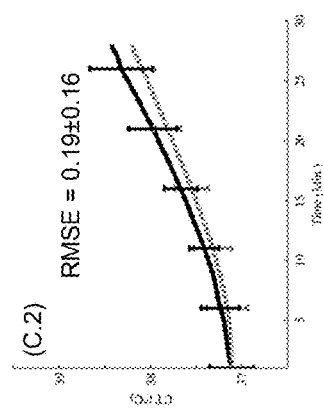
FIG. 8B8
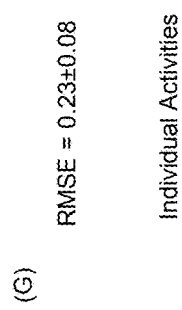
FIG. 8B12
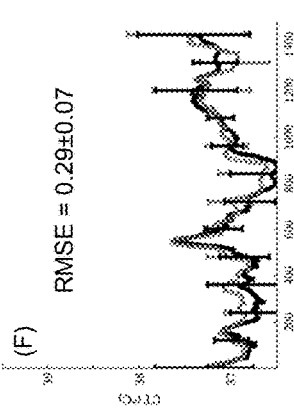
FIG. 8B13
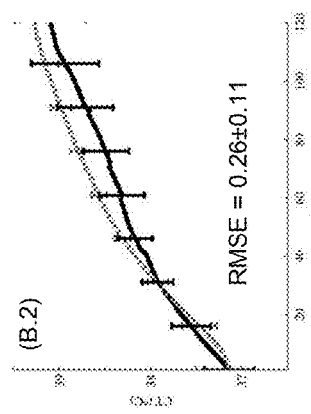
FIG. 8B14
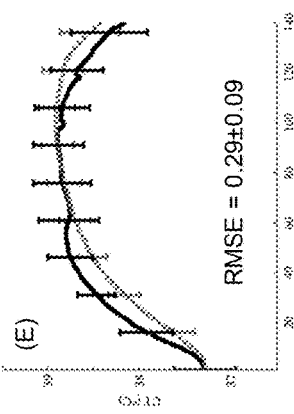
FIG. 8B17
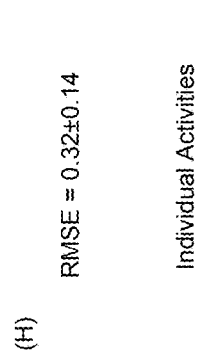
FIG. 8B15
FIG. 8B16
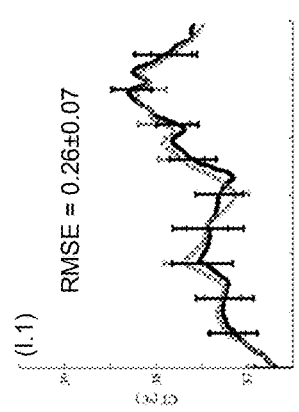
FIG. 8B18

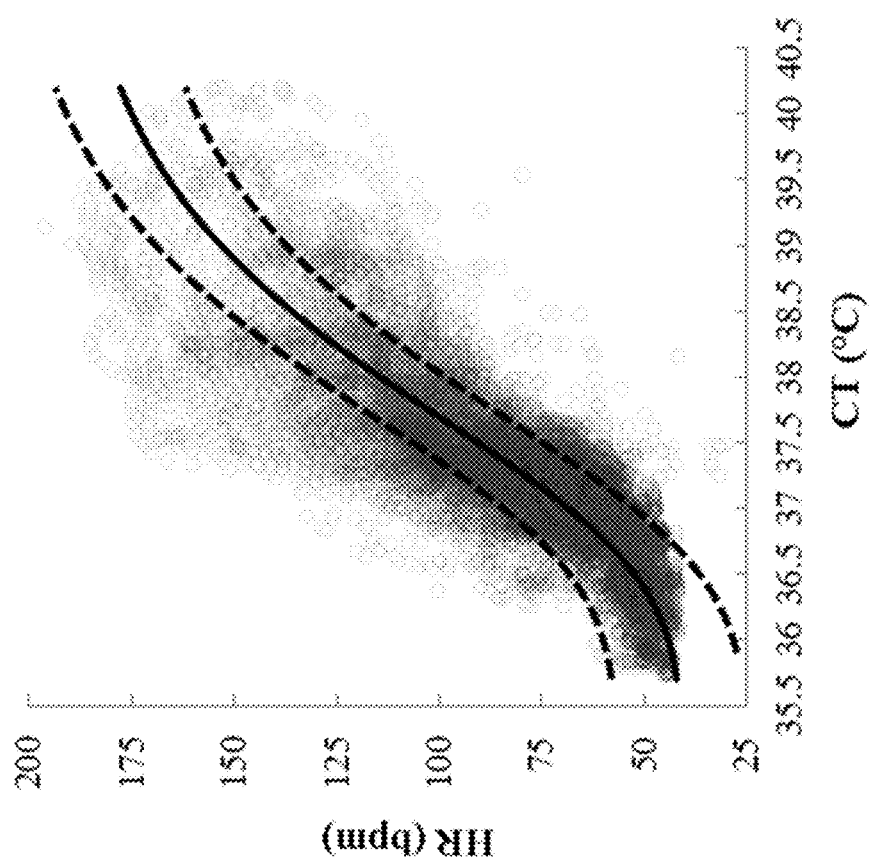
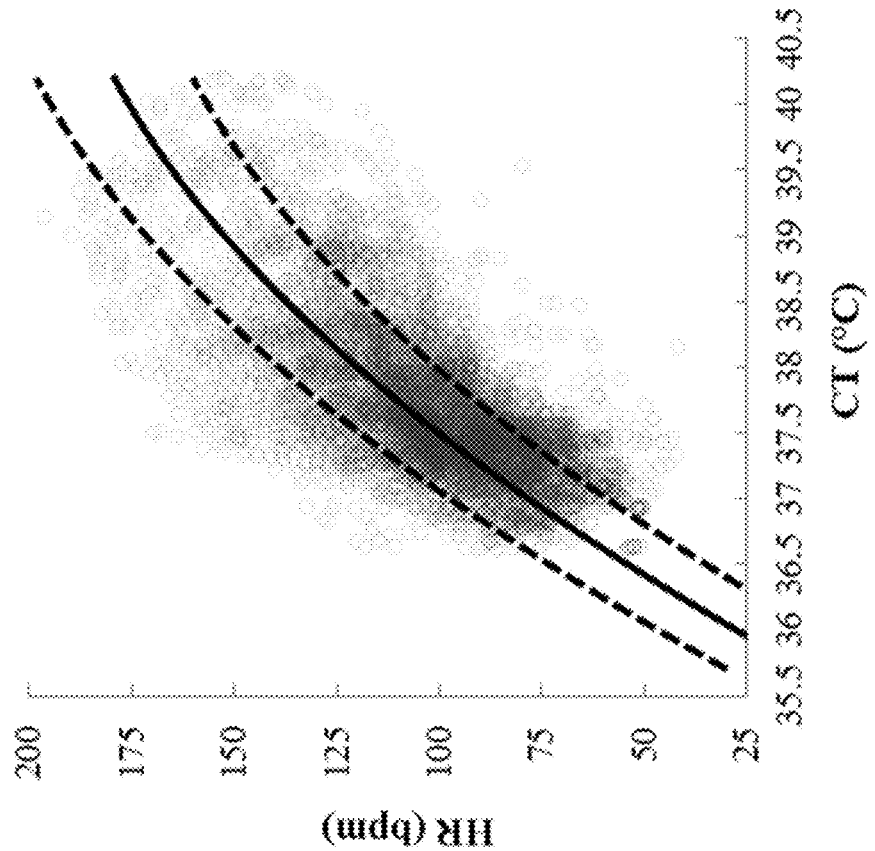

METHOD FOR ESTIMATING CORE BODY TEMPERATURE

CROSS-REFERENCE TO RELATED APPLICATIONS

This application is the National Stage entry of International Application No. PCT/US2020/017136, filed 7 Feb. 2020, which claims the benefit of U.S. Provisional Application Ser. No. 62/802,373, filed 7 Feb. 2019, the contents of which are herein incorporated by reference in their entirety.

STATEMENT AS TO RIGHTS OR INVENTIONS MADE UNDER FEDERALLY SPONSORED RESEARCH AND DEVELOPMENT

This invention was made with government support from the U.S. Army Research Institute of Environmental Medicine, a subordinate organization of the United States Army Medical Research and Materiel Command. The United States government has certain rights in the invention.

FIELD OF THE INVENTION

The invention in at least one embodiment relates to using a person's heart rate to estimate the core body temperature for the person.

BACKGROUND OF THE INVENTION

Continuous ambulatory measurement of core body temperature (CT) can be a critical component of human heat strain assessment during strenuous work (Moran et al 1998; Frank et al 2001). However, while personal physiological monitoring technology has developed to the point where multi-parameter sensor systems can be used to collect data in a variety of settings over extended periods of time, the requisite measurement of core body temperature still remains a challenge.

Medical grade core body temperature measurement using pulmonary arterial blood temperature is only appropriate in a clinical setting. The traditionally accepted laboratory rectal and esophageal probe methods are impractical for ambulatory settings. Other non-invasive methods of estimating core body temperature using external measurements such as axillary or tympanic temperatures have proven unreliable (Lim, Byrne and Lee 2008). Ingestible thermometer pills (e.g., Jonah Pill thermometer, Respironics, Bend, Oreg.) have been used successfully in field settings (e.g. Lee et al 2010), and have been within acceptable limits of agreement (±0.4° C.) and bias (<0.1° C.) when compared to esophageal temperatures (Byrne and Lim 2007). However, these thermometer pills have drawbacks: (1) they cannot be used by all people due to medical contraindications, and (2) they can suffer from inaccuracy when hot or cold fluids are consumed (Wilkinson et al 2008). The difficulty in directly measuring core body temperature in ambulatory settings has led to the search for a practical alternative technique.

One non-invasive approach that has received attention is the zero heat-flux (ZHF) method (Fox et al 1973) where an insulated area of the skin is heated until there is no heat flow. The temperature of the skin is then assumed to be equivalent to deep body temperature. Most of the work on this approach has been in laboratory and clinical settings (Yamakage, Iwasaki and Namiki 2002) with recent work focusing on improving measurement of dynamic temperature changes (Steck, Sparrow and Abraham 2011); decreasing the technique's response time (Teunissen et al 2011); and adapting the ZHF method for use in ambulatory environments (Gunga et al 2008, 2009). In clinical settings these devices have demonstrated good agreement with esophageal measures, while custom sensors developed for ambulatory environments have had varying degrees of success depending on environmental conditions.

Other researchers have used thermoregulatory heat transfer models to estimate core body temperature (Kraning and Gonzalez 1997; Fiala et al 2001; Havenith 2001). These models use an array of input variables that include metabolic rate, environmental parameters, individual characteristics, and clothing parameters (insulation and vapor permeability). In an ambulatory field setting these models suffer from the fact that not all inputs are available all of the time, and measuring or estimating metabolic rate is difficult. Recent work has focused on combining thermoregulatory heat transfer models with metabolic rate estimators that use heart rate with ambient temperature modifiers to account for skin blood flow (Yokota et al 2008). This real-time model provided accurate group-mean core body temperature estimates in a number of different environmental and clothing conditions (Degroot et al 2008). While this method shows promise it still requires many input parameters that must be measured independently from an individual such as environmental conditions and clothing characteristics.

A number of methods have been developed over the years to predict CT from less invasive measures (e.g., heart rate, skin temperature, respiration rate) (Buller at al., 2013; Niedermann et al., 2014; Richmond, Davey, Griggs, & Havenith, 2015) as well as methods to predict CT from estimations, approximations, or actual measures of environmental conditions, clothing, activity, and individual parameters (Potter, Blanchard, Friedl, Cadarette, & Hoyt, 2017). The approaches by both Niedermann et al. (2014) and Richmond et al. (2015) both initially collected a range of measurements and narrowed them down to fewer in order to obtain reasonable estimates of CT while being near-non-invasive. While both approaches use non-invasive measures (e.g., skin temperature, heat flux, heart rate), less involved methods of sensing are more ideal (e.g., single measure/sensor) such as solely heart rate (Buller et al., 2013).

While the majority of estimation methods for CT have focused on stressed environments during exercise conditions, resting CT modeling is useful for research and clinical purposes including circadian rhythm monitoring. Circadian rhythm research has grown considerably over the past two decades (Refinetti, Lissen, & Halberg, 2007) as circadian disturbances have been linked to cancer (Savvidis & Koutsilieris, 2012), neuropsychiatric illness (Jagannath, Peirson, & Foster, 2013), and obesity (Shi, Ansari, McGuinness, Wasserman, & Johnson, 2013). However, implementing traditional CT measurement techniques in free-living settings is difficult. A need exists for an accurate resting CT estimator compatible with free-living settings.

Heart rate (HR)-based CT estimation models have been used to estimate resting CT and circadian rhythms under free-living conditions (Sim et al., 2016). ECTemp™ is a HR-based CT estimation algorithm used mainly as a real-time thermal strain indicator in military populations (Buller at al., 2013; Buller, Tharion, Duhamel, & Yokota, 2015). ECTemp™ demonstrated high accuracy and precision (bias, −0.03±0.32° C.) when validated on over 52,000 observations from 83 volunteers from 9 different studies that involved intense, strenuous activity and heat stress (Buller et al., 2013). U.S. Patent Application Publication No. 2014/

0180027, which is hereby incorporated by reference in its entirety, is directed to ECTemp's original quadratic equation for describing gradual saturation in HR at higher CT.

However, as described in Looney at al., 2017, and Looney et al., 2018, ECTemp™'s original quadratic equation for describing the gradual saturation in HR at higher CT may not adequately model the CT-HR relationship at lower CT. (Looney at al. (Looney, D P, Buller, M J, Gribok, A V, Leger, J L, Potter, A W, Rumpler, W V, Tharion, W J, Welles, A P, Friedl, K E, & Hoyt, R W) (2018), "Estimating Resting Core Temperature Using Heart Rate", *J. for the Measurement of Physical Behaviour,* 1, 79-86, is hereby incorporated by reference in its entirety.) The quadratic equation does not predict CT under 36° C. unless HR drops below physiological limits (<27 bpm). The original development dataset contained few data points at lower CT to maximize CT estimation accuracy during high thermal-work strain (Tharion et al., 2013). ECTemp™ must be adapted to accurately estimate lower CT before it can be examined as a potential CT circadian rhythm estimator.

Retraining ECTemp™ with additional resting CT data may increase accuracy and precision of lower CT estimates. Thus, a need exists for an improved method of estimating CT, wherein such method adequately models the CT-HR relationship at lower CT.

SUMMARY OF THE INVENTION

The inventors have surprisingly discovered that a sigmoid equation better characterizes the saturation in HR at both upper and lower CT compared to the original quadratic equation. The instant disclosure describes and validates a new sigmoid equation for ECTemp™ to better estimate resting CT.

The original ECTemp™ algorithm presented in Buller et al. (2013) utilized an extended Kalman filter (Welch and Bishop 1995, Kalman 1960) to estimate body core temperature (CT, or Tc) from sequential heart rate. The original approach was designed to accurately estimate Tc for exercise in the heat for young fit individuals. While the algorithm was successful for this specific purpose, a number of improvements were made to make the model applicable to all individuals in many additional environments. These adjustments included those for age (younger and older), fitness (to include unfit to athlete), passive heating and cooling, and different rates of change in core temperature during exercise and recovery.

The original ECTemp™ model was designed to fit within a Kalman Filter (KF) framework. A KF framework is comprised of two relationships: a "time-update" model, and an "observation" model. Here an item or variable of interest must be tracked from a series of "noisy" observations, and knowledge of the temporal dynamics. The extended Kalman filter requires two models defined by linear Gaussian probability density functions. One model relates how the variable to be tracked changes over time (i.e., the "time-update" model), while the other model relates current observations to the variable of interest (i.e., the "observation" model).

It was hypothesized that heart rate could be used as a "noisy" observation of core body temperature. Thus, by understanding how core body temperature changes over time and the most likely core body temperature for a given heart rate, an extended Kalman filter model to estimate a series of core body temperature values could be learned. Heart rate is a convenient observation of the expected core body temperature at steady state or a leading indicator of core body temperature as it contains information about both heat production (through the Fick (1855) equation and $VO_2$) and heat transfer since heart rate is related to skin profusion.

In the estimation of core temperature the "time-update" model relates how core temperature changes from time step to time step along with the uncertainty/noise of this change. The "observation" model relates an observation of heart rate to a core temperature value along with the uncertainty of this mapping. The "time-update" and "observation" models are shown in equations (1) and (2) respectively as regression models with the uncertainty/noise represented as zero mean Gaussian distributions with variances of $\gamma^2$ and $\sigma^2$.

$$CT_t = a_1 CT_{t-1} + a_0 + f \text{ Where } f \sim N(0,\gamma) \tag{1}$$

where CT=core temperature, subscript t=time point, $a_1$=time update model coefficient, $a_0$=time update model intercept, f=noise drawn from a Gaussian distribution (N) with mean 0 and SD $\gamma$. Parameters $a_1$ and $a_0$ were found by least squares regression of $CT_t$ by $CT_{t-1}$. The parameter $\gamma$ was derived from the standard deviation (SD) of the discrete probability distribution of delta CT points from the development data.

$$HR_t = b_2 CT_t^2 + b_1 CT_t + b_0 + g \text{ Where } g \sim N(0,\sigma) \tag{2}$$

FIGS. 5A and 5B show the original "time-update" model (FIG. 10A) and the "observation" model (FIG. 10B).

Core body temperature can be estimated by an extended Kalman filter model in at least one embodiment using a single parameter, heart rate, to within similar bias and limits of agreement seen when comparing rectal and esophageal measurements of core temperature. The model is demonstrated to perform similarly in different environments, in the presence of dehydration, with limited or complete clothing occlusion, and whether volunteers are heat acclimated or not. While this technique is not a replacement for direct core temperature measurement, it offers an approach for estimating individual core temperature and is accurate and practical enough to provide a means of real-time heat illness risk assessment.

The invention in at least one embodiment includes a method for determining the core body temperature of a person where the method includes determining an initial core body temperature and heart rate of said person; providing the initial core body temperature and heart rate of the person to a processor; and calculating a predicted core body temperature by the processor using an extended Kalman filter based on the heart rate and the initial core body temperature. In a further embodiment, the method further includes receiving a new heart rate of the person with the processor; calculating a new predicted core body temperature using the extended Kalman filter based on the new heart rate and a most recent predicted core body temperature; and repeating the receiving a new heart rate and calculating a new predicted core body temperature at predetermined intervals. In a further embodiment, the method further includes when the new predicted core body temperature exceeds a predetermined threshold, sending an alarm signal prior to proceeding to repeating, wherein in a further method the alarm signal triggers an alarm; and when the new predicted core body temperature does not exceed a predetermined threshold, proceeding to repeating. In a further embodiment to any of the above embodiments, the method further includes obtaining the predetermined interval. In a further embodiment to any of the above embodiments, providing the predicted core body temperature includes displaying the predicted core body temperature and/or transmitting the predicted core body temperature with a transmitter to an external device.

In a further embodiment to any of the above embodiments, calculating a predicted core body temperature includes calculating a preliminary core body temperature; calculating a preliminary estimate of the variance of a core body temperature estimate; calculating an extended Kalman filter mapping function variance coefficient; calculating a Kalman gain weighting factor based on the preliminary estimate of variance and the extended Kalman filter variance coefficient; and calculating the predicted core body temperature using a preliminary time-update estimate, an error between the new heart rate and an expected heart rate given the preliminary estimate of the core body temperature. In a further embodiment, calculating a predicted core body temperature further includes determining a variance of the predicted core body temperature.

In a further embodiment to any of the above embodiments, the method further includes adjusting the extended Kalman filter based on at least one of a fitness level, an age, a maximum heart rate and a resting heart rate of the person.

In a further embodiment to any of the above embodiments, the invention includes a system for performing the method.

The invention according to at least one embodiment, the system including a heart rate data source that comprises or is capable of comprising heart rate data from one or more persons; and a processor in communication with said heart rate data source, said processor capable of calculating a core body temperature of at least one person based on one or more predetermined constants, and wherein said processor comprises heart rate information and most recent core body temperature data as inputs, optionally as the only inputs thereof. In a further embodiment, the system further includes a display in communication with said processor. In a further embodiment to any of the above system embodiments, the system further includes a transmitter for communication with an external system, said transmitter in communication with said processor. In a further embodiment to any of the above system embodiments, the system further includes a temperature sensor in communication with said processor.

In a further embodiment to any of the above system embodiments, the processor includes an initial core body temperature module for determining an initial core body temperature, a heart rate module for determining heart rate information, and a core body temperature calculator in communication with said initial core body temperature module and said heart rate module. In a further embodiment to the prior embodiment, the processor further includes a timer module in communication with said heart rate module and said core body temperature calculator. In a further embodiment to the prior embodiment, the processor further includes an alarm module in communication with said core body temperature calculator.

In a further embodiment to any of the above system embodiments, the system further includes a display in communication with said core body temperature calculator; a transmitter in communication with said core body temperature calculator; and a temperature sensor in communication with at least one of said timer module and said alarm module. In an alternative embodiment, at least one of the display, the transmitter, and the temperature sensor is omitted.

The invention according to at least one embodiment, the system including a heart rate data source; and a processor in communication with said heart rate data source, said processor having program code embodied therewith, the program code executable by the processor to set or determine an initial core body temperature; receive a heart rate of the person; calculate a predicted core body temperature using an extended Kalman filter having as inputs the heart rate and the initial core body temperature; and provide the predicted core body temperature. In a further embodiment, the system further includes at least one of a display in communication with said core body temperature calculator; and a transmitter in communication with said core body temperature calculator. In a further embodiment to either of the previous two embodiments, the initial core body temperature is set based on the initial heart rate of the person.

BRIEF DESCRIPTION OF THE DRAWINGS

FIG. 1 illustrates a method according to at least one embodiment of the invention.

FIG. 2 illustrates a method according to at least one embodiment of the invention.

FIGS. 3A-3E illustrate respective systems according to at least one embodiment of the invention.

FIGS. 4A1 and 4B1 illustrate panels showing mean observed (obs.) and estimated (est.) Tcore responses and FIGS. 4A2 and 4B2 illustrate panels for Bland Altman charts for the validation Elite distance runner data for a five mile run completed at <6 minute/mile pace.

FIGS. 4A1 and 4A2 show the Kalman filter model output using the original Tcore variance $\gamma=0.024$. FIGS. 4B1 and 4B2 show the Kalman filter response using the variance learned from the Elite runner development data $\gamma=0.043$. Error bars represent ±1 standard deviation (SD). The Bland Altman charts in FIGS. 4A2 and 4B2 show arithmetic mean (solid horizontal line), ±2 SD (dashed horizontal lines), and ±5° C. zone (gray box).

FIG. 5A shows the time update model represented as a discrete probability distribution found from the development data.

FIG. 5B shows the observation model as a scatter plot of development data points showing mean heart rate (HR) by core body temperature (CT)±SD the optimal CT-HR line segment points (Line Segment) and the CT to HR mapping function (Fit).

FIGS. 8A1-8A18 show Bland Altman plots showing bias (solid) and ±1.96 SD (dashed) for the various studies discussed in this disclosure. The parentheticals present in these figures correspond to the studies discussed herein.

FIGS. 8B1-8B18 show the mean observed core body temperature (solid—black) and mean estimated core body temperature (dashed—gray) with ±1 SD for the various studies discussed in this disclosure. The means for studies G (FIG. 8B15) and H (FIG. 8B16) are not shown as they are a combination of several activities over the study period. *=end points significantly different p<0.05. The parentheticals present in these figures correspond to the studies discussed herein.

FIGS. 10A and 10B show original ECTemp training data (FIG. 10A) with the original quadratic relationship for the extended Kalman Filter "Observation" model, and the same training data with the addition of rest and sleep data (FIG. 10B) showing the sigmoid extended Kalman Filter "Observation" model. Solid line, trend line for mean HR; Dotted lines, M±SD.

DETAILED DESCRIPTION

Figure 3B:
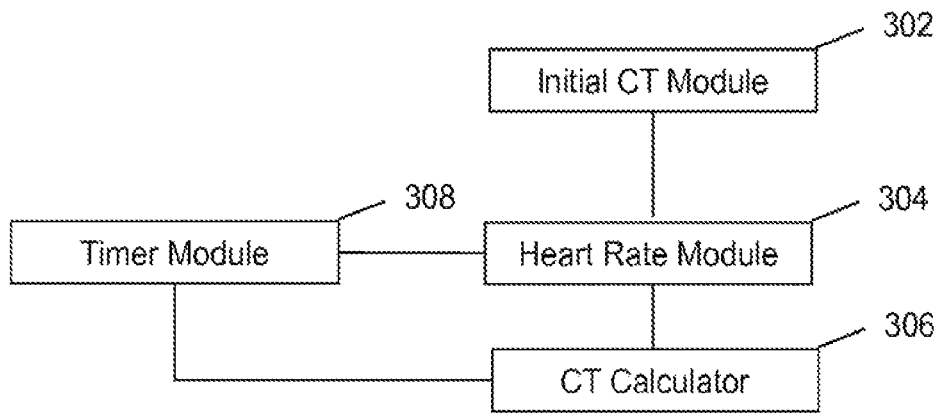

In at least one embodiment, a system and/or method is provided to estimate a person's core body temperature using the person's current heart rate. In a further embodiment, the previous core body temperature is also used. In at least one embodiment the relationship between core body temperature and heart rate is a sigmoid relationship that varies over a range of heart rate measurements, where in at least one embodiment the heart rate measurement range is between 50 and 180 and in a further embodiment, the maximum heart rate is set to 220 minus the person's age with a corresponding scaling of the sigmoid relationship. The sigmoid relationship provides a more accurate estimate of the core body temperature at (1) higher heart rates than previously estimated using prior linear curve fits, and (2) lower core temperatures than previously estimated using prior quadratic equation fits. In a further embodiment, the system and method use an extended Kalman filter model to determine the core body temperature.

FIG. 1 illustrates a high level method embodiment as a flowchart of operation of at least one system embodiment. Setting (or receiving) an initial core body temperature for a person, 105.

Examples of how the initial core body temperature can be set include 1) a predetermined resting core body temperature for that person; individuals with similar physical characteristics of the person such as height, weight, and age; and a preset value, 2) based on an initial heart rate reading for the person, and 3) combination of the two. Examples of sources of the heart rate include a heart rate monitor attached to the person, a processor receiving EKG signals from electrodes attached to the person, a processor receiving a photoplethysmogram signal (e.g., a pulse oximeter), or a processor receiving a ballistic-cardiogram signal.

Receiving a new heart rate for the person, 110. In at least one embodiment, the new heart rate is obtained from the same source from which the initial heart rate is obtained.

Calculating a predicted core body temperature for the person based on the most recent heart rate and the previous core body temperature for the person, 115.

Providing the predicted core body temperature, 120. In at least one embodiment, examples of providing include, but are not limited to, transmitting (or outputting) to an external device, displaying on a display, recording in memory, inputs to a health assessment algorithm. Examples of an external device include, but are not limited to, a processing hub on the person, a smartphone, a computer, and a computer network.

Repeating the receiving (110), calculating (115) and providing (120) steps on a predetermined schedule. Examples of a predetermined schedule include 1 minute intervals, 2 minute intervals, 5 minute intervals, and 10 minute intervals, and in a further embodiment, the intervals are any interval between 30 seconds and 10 minutes. In a further embodiment, the method further includes setting (or selecting) the predetermined interval prior to calculating the predicted core body temperature for the first time. In at least one further embodiment, a timer is used to delay the repeat cycle after providing the predicted core body temperature.

In a further embodiment, the predicted core body temperature is calculated in a multi-step process using an extended Kalman filter model based on experimental data.

In a further embodiment to the above embodiments, the predicted core body temperature is calculated using the method illustrated in FIG. 2. Calculating a core body temperature preliminary estimate ($\hat{C}T_t$) based upon the previous core body temperature estimate ($CT_{t-1}$) and the time-update mapping function ($a_1$ and $a_0$), 205. An example equation is as follows:

$$\hat{C}T_t = a_1 \cdot CT_{t-1} + a_0 \qquad (3)$$

Where CT=core temperature, subscript t=time point, $a_1$=time update model coefficient, and $a_0$=time update model intercept. Calculating a preliminary estimate of the variance of the core body temperature estimate ($\hat{v}_t$) based upon the previous core body temperature variance ($v_{t-1}$) the time-update mapping function ($a_1$) and variance ($\gamma^2$), 210. An example equation is as follows:

$$\hat{v}_t = a_1^2 \cdot v_{t-1} + \gamma^2 \qquad (4)$$

Calculating the extended Kalman filter mapping function variance coefficient, 215. An example equation is as follows:

$$c = 2 \cdot b_2 \hat{C}T_t + b_1 \qquad (5)$$

where $b_2$=observation model quadratic coefficient, $b_1$=observation model coefficient, and $b_0$=observation model intercept. Calculating the Kalman gain ($k_t$) weighting factor based on the preliminary estimate of variance and using the extended Kalman filter variance coefficient, 220. An example equation is as follows:

$$k_t = \frac{\hat{v}_t c_t}{c_t^2 \hat{v}_t + \sigma^2} \qquad (6)$$

Calculating the final estimate of $CT_t$ using the preliminary time-update estimate, the error between the heart rate ($HR_t$)

observation and the expected heart rate given the preliminary estimate of CT, 225. An example equation is as follows:

$$CT_t = \hat{C}T_t + k_t\{HR_t - (b_2 \cdot \hat{C}T_t^2 + b_1 \cdot \hat{C}T_t + b_0)\} \quad (7)$$

Determining the variance of the final core body temperature estimate ($v_t$). An example equation is as follows:

$$v_t = (0 - k_t c_t)\hat{v}_t \quad (8)$$

In a further embodiment, the previous embodiment is reduced by consolidating equations 3-6 into equations 7 and 8 to provide a calculating step. Based on this disclosure, it should be understood that the level of consolidation can be any point between the last two embodiments.

The following example of equations 2-8 are based on experimental data, which will be discussed in more detail later in this disclosure, and the use of a time period of one minute. Equation 3 simplifies as follows:

$$\hat{C}T_t + a_1 \cdot CT_{t-1} + a_0 = 1 \cdot CT_{t-0} + 0$$

$$\hat{C}T_t = CT_{t-1} \quad (3)$$

Equation 4 simplifies by setting the time-update mapping function ($a_1$) to 1 and the variance (or Gamma) ($\gamma^2$) to $0.022^2$. Equation 4 simplifies as follows:

$$\hat{v}_t = a_1^2 \cdot v_{t-1} + \gamma^2 = 1 \cdot v_{t-1} + 0.022^2$$

$$\hat{v}_t = v_{t-1} + 0.000484 \quad (4)$$

Equation 5 simplifies by setting $b_0 = -7887.1$, $b_1 = 384.4286$, and $b_2 = -4.5714$. Equation 5 becomes:

$$c = 2 \cdot b_2 \hat{C}T_t + b_1 = 2 \cdot -4.5714 \cdot \hat{C}T_t + 384.4286$$

$$c_t = -9.1428 \cdot \hat{C}T_t + 384.4286 \quad (5)$$

Equation 6 simplifies by setting a to 18.88, which is representative of the mean standard deviation for the binned heart rate from the experimental data. Equation 6 becomes:

$$k_t = \frac{\hat{v}_t c_t}{c_t^2 \hat{v}_t + \sigma^2} = \frac{\hat{v}_t c_t}{c_t^2 \hat{v}_t + 18.88^2} \quad (6)$$

$$k_t = \frac{\hat{v}_t c_t}{c_t^2 \hat{v}_t + 356.4544}$$

Using the prior variables, equation 7 simplifies as follows:

$$CT_t = \hat{C}T_t + k_t\{HR_t - (b_2 \cdot \hat{C}T_t^2 + b_1 \cdot \hat{C}T_t + b_0)\}$$

$$CT_t = \hat{C}T_t + k_t\{HR_t - (-4.5714 \cdot \hat{C}T_t^2 + 384.4286 \cdot \hat{C}T_t + 7887.1)\} \quad (7)$$

In at least one embodiment as illustrated, for example, in FIG. 3A, the above discussed method embodiments are performed on a processor 300 running code that enables the performance of at least one method embodiment and is in communication with a heart rate data source 310. Examples of a heart rate data source include, but are not limited to, a heart rate monitor attached to the person, a processor receiving EKG signals from electrodes attached to the person, a processor receiving a photoplethysmogram signal (e.g., a pulse oximeter), or a processor receiving a ballistic-cardiogram signal. In at least one embodiment, there is a memory or storage (not illustrated) in communication with the processor 300.

In at least one embodiment as illustrated, for example, in FIG. 3B, the processor 300 includes code that will run a set of modules including an initial core body temperature (CT) module 302, a heart rate module 304, and core body temperature calculator 306. The initial body temperature module 302 sets or receives an initial core body temperature using the different approaches discussed above. The heart rate module 304 in at least one embodiment receives a heart rate from an external source, or alternatively processes received signals from the external source to determine the current rate for the person. In a further embodiment, the heart rate module 304 is a heart rate monitor that the system has been incorporated into to provide the additional functionality of the invention. The core body temperature calculator 306 determines the predicted core body temperature for the person based on the prior core body temperature and the current heart rate.

Figure 3C:
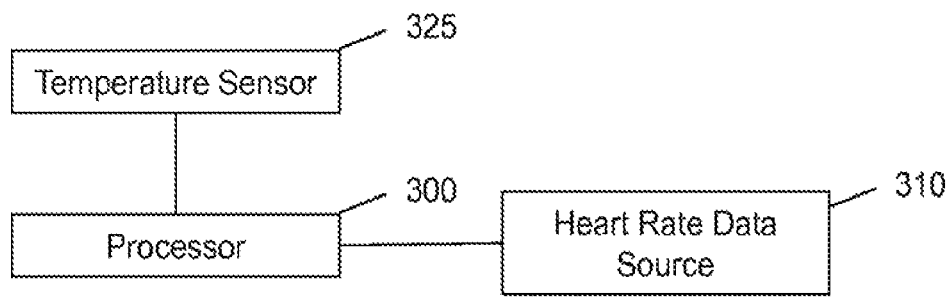

Also illustrated in FIG. 3B is an optional component of a timer module 308 that provides the sampling rate at which the heart rate is determined and the core body temperature is calculated. The timer module (or timer) 308 uses a predetermined time period prior to the start of a session for calculating a core body temperature. In an alternative embodiment, the predetermined time period is set by a user. In a further alternative embodiment, the predetermined time period is stored in a memory or other storage, for example, in a database or is present in the code running on the processor. In a further embodiment, the timer module 308 is connected to a temperature sensor 325 connected to the processor as illustrated, for example, in FIG. 3C. The timer adjusts the sampling intervals based on the temperature signal provided by the temperature sensor 325 by decreasing the interval when the temperature is above a predetermined threshold(s). In at least one embodiment, the temperature sensor 325 detects the environment temperature, while in another embodiment it detects the temperature proximate the skin of the person. In a still further embodiment, there are two of temperature sensors to detect both temperatures.

Figure 3D:
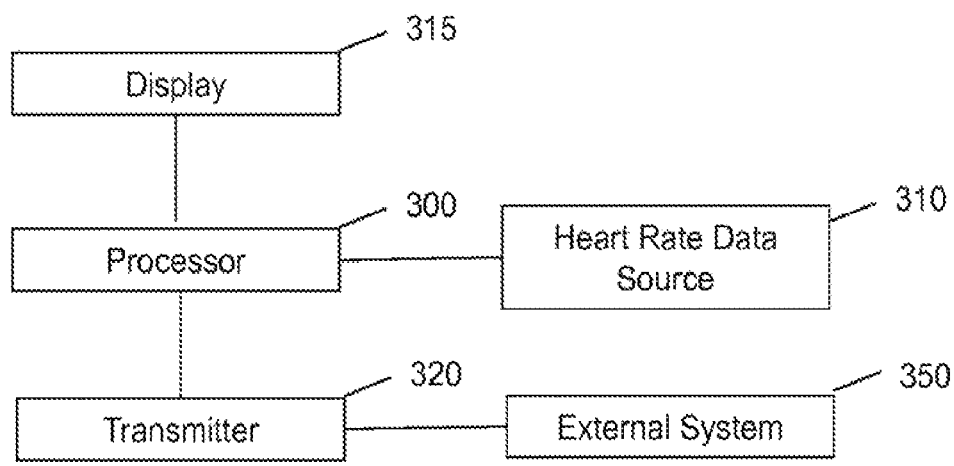

In further embodiments, the processor is present on a heart rate monitor and/or a processing hub worn by the person whose core body temperature is being monitored. In a further embodiment as illustrated, for example, in FIG. 3D, the processor 300 is connected to a transmitter 320 to transmit at least the estimated core body temperature to an external system 350. In an alternative embodiment or in addition to the further embodiment, the estimated core body temperature is displayed for viewing by the person being monitored, for example, on a display 315 present on the device with the processor, a wrist worn display, a smart telephone, or a heads up display.

Figure 3E:
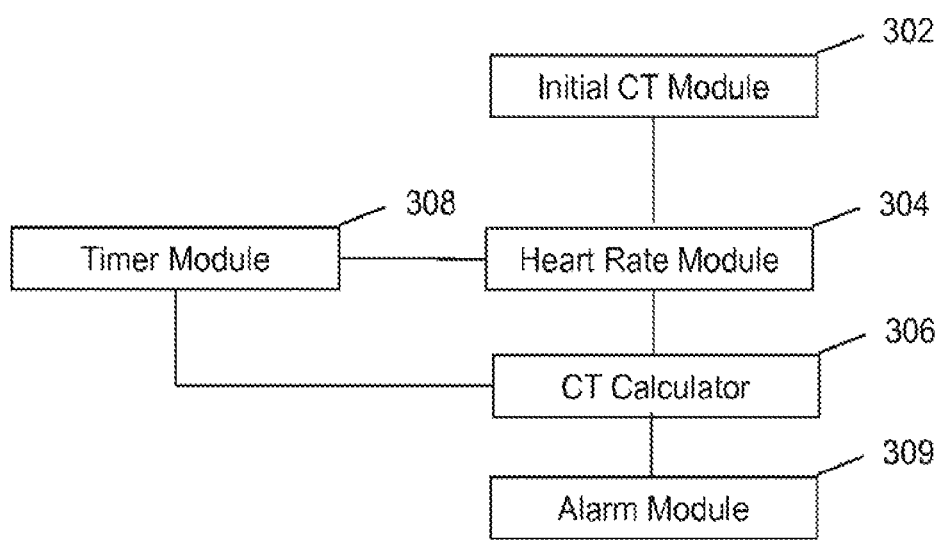

In an alternative embodiment to any of the above embodiments, the system further includes an alarm module 309 (illustrated, for example, in FIG. 3E) as part of the processor for providing an alert signal when predetermined thresholds for the core body temperature are reached. In at least one embodiment, the predetermined thresholds are stored in a memory or other storage, for example, in a database or are present in the code running on the processor. The alert signal triggers an alarm in the system and/or an external device to provide notice of potential risk of overheating of the person. In a further embodiment, the alarm module 309 is in communication with the temperature sensor 325 and uses the detected temperature to select the threshold sets for triggering an alarm such that the threshold sets will set lower temperature thresholds for higher detected temperatures detected by the temperature sensor 325.

In a further embodiment, the processor is detached from the person being monitored and is present in external equipment such as a medical monitor or a computer running software that performs according to at least one method embodiment. In such an embodiment, the information is being provided to a system and/or an individual other than the person being monitored. Examples of how the information is provided include, but are not limited to, transmitting over a cable and/or wirelessly through a transmitter and a receiver, and a user interface such as a keyboard or graphical interface displayed on a display. Although in a further embodiment, the estimated core body temperature is also provided to the person being monitored, for example, for displaying as discussed previously.

In an alternative embodiment, the extended Kalman filter model is adjusted for fitness level, because it is expected that as fitness levels deviate from the training data that the model's performance would degrade. In response to this potential, one of the model parameters can be modified to account for deviations in fitness levels in an alternative embodiment. In particular, the Gamma (or variance) parameter from Equation 4 is adjusted by increasing it for better fitness, and decreasing it for lower fitness levels. It is believed that a linear relationship will exist where Gamma will equal a fitness value added to a constant where the fitness value may equal a coefficient times a fitness number for that person.

To test the hypothesis of a variance based on fitness level for the difference in core body temperature ($\Delta$Tcore) time-update conditional Gaussian PDF was learned from the Elite distance runner development data (Ely et al. 2009) then tested on the remaining hold-out elite distance runner data (n=12). FIGS. 4A and 4B shows a time series plot and Bland Altman deviation plot for the core body temperature (Tcore) and extended Kalman filter model estimates from the Elite distance runners held out to be used as validation data. FIG. 4A shows the mean core body temperature (Tcore) and model estimates, using the core body temperature (Tcore) variance learned from the original development and tuning data ($\gamma$=0.024), and FIG. 4B shows the responses using the variance learned from the Elite development data ($\gamma$=0.043).

In a further alternative embodiment, the extended Kalman filter model is adjusted for the resting heart rate based on, for example, an initial heart rate measurement received from the heart rate monitor. The initial heart rate will be used to move the graph illustrated, for example, in FIG. 5B up or down from the lower heart rate in a linear manner. Or in an alternative approach, the bottom heart rate will be adjusted up or down based on the initial heart rate while the top heart rate will not be adjusted but instead the correlation between the heart rate and the core body temperature will be scaled.

In a further alternative embodiment, the Kalman filter model is adjusted based on age of the person by adjusting the maximum heart rate used in the model to reflect the person's age. An example of one way to determine maximum heart rate is to use 220 minus the person's age; however, the maximum heart rate could be determined for the person based on physiological testing prior to use of the model. In at least one embodiment, the maximum heart rate is adjusted to reflect the heart rate for the person while leaving the starting heart rate in the model alone and thereby adjusting the scale of the correlation between the heart rate and the core body temperature.

In a further alternative embodiment, any combination of the fitness, resting heart rate, and maximum heart rate are used to fine-tune the model for the individual.

A. Model Verification for the Extended Kalman Filter Model of Equations 3-8

Data from ten laboratory and field studies with a total of 100 test volunteers were used in the development (N=17) and validation (N=83) of the extended Kalman filter model discussed above in connection with Equations 3-8. Original data from the studies were used in consultation with the principal investigators of these studies. These studies are described in detail in their original cited publications. All research was conducted under the oversight of respective Institutional Review Boards. In some instances, the number of volunteers used for the analyses was less than those reported in the cited studies. These instances occur where either the heart rate and/or core body temperature data were not available for these participants from the original research data or where volunteers failed to complete the whole experiment. Table 1 discussed later contains a summary of study volunteers, work rates, and environmental conditions where the study is identified by letter code (T and A-I).

Model Development Data (T): heart rate (Equivital EQ02, Hidalgo Cambridge UK) and core body temperature (ingested—Jonah Thermometer Pill, Respironics, Bend, Oreg.) data were collected from seventeen male U.S. Army volunteers (age=23±4 years, height=1.79±0.08 m, weight=81.3±10.8 kg, body fat=18±3% mean±standard deviation (SD)) on one of two days of a field training exercise during July 2011 (air temperature 24°-36° C., 42%-97% relative humidity (RH), wind speeds from 0 to 4 ms$^{-1}$ (meters per second) with activities during the day conducted under full sun) at Fort Bragg, N.C. The field exercise included periods of sleep, rest, foot movement and periods of vigorous upper body work, providing a very wide range of work rates. These data were chosen to develop the model as they included the largest range (36-40° C.) and most dynamic core body temperature responses of our analyzed data.

Data from nine studies were used to examine the performance of the model in a number of different conditions and to provide model validation. Where studies had different test conditions, these conditions are further labeled and summarized in Table 2 after the discussion of the studies. Four laboratory studies were used for controlled comparisons of the effects of different environments, hydration states, clothing ensembles, and acclimation state; and five field physiological monitoring experiments were used to examine the performance under different climates and different levels of protective clothing.

Laboratory Study (A) Environmental Conditions (Cheuvront et al 2007): eighteen volunteers (seventeen male, one female) (22±4 years, 1.77±0.04 m, 80.9±15.3 kg) participated in six eight-hour bouts of intermittent treadmill exercises while wearing U.S. Army battledress uniform (BDU). Volunteers were euhydrated and heat acclimated. Core body temperature was measured using a thermometer pill suppository. The six test conditions were: (A.1) 20° C., 50% RH and a total energy expenditure (TEE) rate of about 460 W; (A.2) 27° C., 40% RH and a TEE rate of about 350 W; (A.3) 27° C., 40% RH and a TEE rate of about 470 W; (A.4) 35° C., 30% RH and an TEE rate of about 350 W; (A.5) 35° C., 30% RH and a TEE rate of about 470 W; and (A.6) 40° C., 40% RH and a TEE rate of about 360 W.

Laboratory Study (B) Hydration State (Montain & Coyle 1992): eight heat acclimated male volunteers (23±3 years, 71.9±11.6 kg) completed two hours of cycle ergometer exercise at a TEE rate of about 1000 W while wearing shorts and a t-shirt in environmental conditions of 33° C., 50% RH. Core body temperature was measured with a rectal probe. Conditions were: (B.1) hydrated with 80% fluid replacement; and (B.2) dehydrated with no fluid replacement.

Laboratory Study (C) Clothing (Latzka et al 1997; 1998): eight heat acclimated euhydrated male volunteers (23±6 years, 1.76±0.06 m, 76.0±15.1 kg, 18±6% body fat) participated in treadmill exercise at TEE rates of about 675 W in an environment of 35° C. and 55% RH. Core body temperature was measured with a rectal probe. Conditions were: (C.1) shorts and a t-shirt (n=6) for 111 minutes of exercise; and (C.2) totally encapsulating chemical protective clothing (n=8) for 28 minutes of exercise.

Laboratory Study (D) Acclimation State (Kenefick et al 2011): seven male euhydrated volunteers (24±7 years, 1.78±0.08 m, 80.2±21.3 kg, 16±11% body fat) participated in a treadmill exercise at a TEE rate of about 550 W while wearing shorts and a t-shirt in environmental conditions of 45° C., 20% RH. Core body temperature was measured using a thermometer pill used as a suppository. Conditions were: (D.1) unacclimated for 59 minutes of exercise; and (D.2) acclimated (10 previous days of exercise in the heat) for 100 minutes of exercise.

Field Study (E) U.S. Army Ranger Training Brigade (RTB) (Unpublished): eleven male acclimated euhydrated RTB students (27±6 years, 1.77±0.05 m, 81.7±5.3 kg, 14±3% body fat) participated in an eight mile timed road march (140 minutes) while carrying about 35 kg at night. Volunteers wore the Army combat uniform, and had TEE rates of about 675 W in 25° C., 85% RH environmental conditions with wind speeds ranging from 0 to 3 $ms^{-1}$. Core body temperature was measured by ingested thermometer pill.

Field Study (F) U.S. Special Forces (Buller et al 2011b): seven male heat acclimated euhydrated Special Forces military students (27±2 years, 1.78±0.08 m, 85.7±6.2 kg) who were participating in multi-day selection course were studied. Volunteers were studied over a 24 hour period which included various training activities and sleep. Volunteers wore the Army combat uniform and had average TEE rates about 200 W. Environmental conditions ranged from 9° to 13° C. and 83 to 95% RH with wind speeds of 0.4 to 3.0 $ms^{-1}$ with some sun during outdoor activities. Core body temperature was measured by ingested thermometer pill.

Field Study (G) Iraq (Buller et al 2008): eight male heat acclimated euhydrated U.S. Marines (21±1 years, 1.80±0.07 m, 85.1±9.0 kg, 15±3% body fat) who conducted one of two foot patrols (209 minutes and 250 minutes) in Iraq were studied. Volunteers wore the standard Marine Corps combat shirts and body armor (about a 37 kg load) and had an average TEE rate of about 200 W. Environmental conditions were 42° to 47° C. and 9% to 11% RH; and 39° to 44° C., and 9° to 13% RH with wind speeds <2.0 $ms^{-1}$. Both patrols were conducted in full sun. Core body temperature was measured by ingested thermometer pill.

Field Study (H) Afghanistan (Buller et al 2011a): eight male heat acclimated U.S. Marines (21±2 years, 1.84±0.04 m, 85.7±6.2 kg, 16±3% body fat) who conducted one of two foot patrols during a full mission day in Afghanistan were studied (683 minutes and 488 minutes). Volunteers wore the standard Marine Corps combat shirts and body armor (about 32 kg load). Patrols were conducted with average TEE rates about 400 W. Environmental conditions were 20°±3° C., and 20±11% RH with wind speeds of 2.4±0.8 $ms^{-1}$; and 20°±5.3° C., 26±13% RH with wind speeds of 2.0±1.1 $ms^{-1}$. Both monitoring periods were under full sun. Core body temperature was measured by ingested thermometer pill.

Field Study (I) Australian Army Soldiers (Unpublished): eight male heat acclimated euhydrated Australian Army Soldiers (28±6 years, 1.95±0.09 m, 85.7±14.2 kg, 13±4% body fat) participated in two training activities. Conditions were: (I.1) a simulated patrol and ambush (15°-20° C., 65%-85% RH, wind speed less than 1.5 $ms^{-1}$, limited sun) which included periods of strenuous activity (297 minutes) with the volunteers wearing chemical biological protective gear in an open configuration (Military Operational Protective Posture (MOPP) II); and (I.2) a 5 km road march conducted in fully encapsulating chemical biological protective equipment worn in the MOPP IV configuration (18° C., 72% RH, wind speed <1 $ms^{-1}$, dusk) with an average TEE rate of about 685 W (244 minutes). Core body temperature was measured by ingested thermometer pill.

Table 1 shows the volunteer characteristics, TEE rate and environment summary by study.

TABLE 1

| Study | Time (min.) | n | Age (years) | Height (m) | Wt. (kg) | Body Fat (%) | TEE Rate (W)† | Air Temp. (° C.) | RH (%) |
|---|---|---|---|---|---|---|---|---|---|
| T | ~840 | 17 | 23 ± 4 | 1.79 ± 0.08 | 81 ± 11 | 18 ± 3 | Various | 24-36 | 42-97 |
| A | ~480 × 6 | 18* | 22 ± 4 | 1.77 ± 0.04 | 81 ± 15 | N/C | 350-470 | 20-40 | 30-50 |
| B | 121/121 | 8 | 23 ± 3 | N/C | 72 ± 12 | N/C | 1000 | 33 | 50 |
| C | 111/28 | 6/8 | 23 ± 6 | 1.76 ± 0.06 | 76 ± 15 | 18 ± 6 | 675 | 35 | 55 |
| D | 59/100 | 7 | 24 ± 7 | 1.78 ± 0.08 | 80 ± 21 | 16 ± 11 | 550 | 45 | 20 |
| E | 140 | 11 | 27 ± 6 | 1.77 ± 0.05 | 82 ± 5 | 14 ± 3 | 675 | 25 | 85 |
| F | 1441 | 7 | 27 ± 2 | 1.78 ± 0.08 | 86 ± 6 | N/C | 200 | 9-13 | 83-95 |
| G | 209 + 250 | 8 | 21 ± 1 | 1.80 ± 0.07 | 85 ± 9 | 15 ± 3 | 200 | 39-47 | 9-13 |
| H | 683 + 488 | 8 | 21 ± 2 | 1.84 ± 0.04 | 86 ± 6 | 16 ± 3 | 400 | 20 | 20-26 |
| I | 297/244 | 8 | 28 ± 6 | 1.95 ± 0.09 | 86 ± 14 | 13 ± 4 | Var./685 | 15-20 | 65-85 |

TEE = Total energy expenditure rates.

†Values reported are approximate.

T = Training/Development Data.

*Includes one female.

N/C = Not Collected.

Var. = various.

Means ± SD.

Table 2 shows the mean RMSE, bias, and limits of agreement (LoA) for validation data.

TABLE 2

| Study | Condition | # min. | n | RMSE | Bias | LoA |
|---|---|---|---|---|---|---|
| A.1. Environment | 20° C., 50% RH, 460 W | 507 | 9 | 0.32 ± 0.16 | −0.12 ± 0.33 | ±0.65 |
| A.2 | 27° C., 40% RH, 350 W | 461 | 11 | 0.25 ± 0.14 | −0.09 ± 0.27 | ±0.53 |
| A.3 | 27° C., 40% RH, 470 W | 461 | 10 | 0.32 ± 0.13 | 0.07 ± 0.33 | ±0.65 |
| A.4 | 35° C., 30% RH, 350 W | 461 | 12 | 0.33 ± 0.18 | −0.25 ± 0.28† | ±0.54 |
| A.5 | 35° C., 30% RH, 470 W | 461 | 7 | 0.25 ± 0.12 | 0.07 ± 0.26 | ±0.52 |
| A.6 | 40° C., 40% RH, 360 W | 461 | 7 | 0.29 ± 0.09 | 0.00 ± 0.30 | ±0.60 |
| B.1. Hydration | Hydrated | 121 | 8 | 0.44 ± 0.19† | 0.31 ± 0.36 | ±0.71† |
| B.2 (33° C., 50%) | Hypohydrated | 121 | 8 | 0.26 ± 0.11 | 0.14 ± 0.24 | ±0.48 |
| C.1. Clothing | Shorts & T Shirt | 111 | 6 | 0.21 ± 0.11 | 0.05 ± 0.23 | ±0.45 |
| C.2 (35° C., 55%) | Chem. Bio. PPE | 28 | 8 | 0.19 ± 0.16 | −0.12 ± 0.21 | ±0.40 |
| D.1. Acclimation | Heat Acclimated | 59 | 7 | 0.28 ± 0.11 | −0.13 ± 0.27 | ±0.52 |
| D.2 (45° C., 20%) | Unacclimated | 100 | 7 | 0.26 ± 0.19 | −0.01 ± 0.31 | ±0.60 |
| E. U.S. Army Rangers (24° C., 85%) | | 140 | 11 | 0.29 ± 0.09 | −0.06 ± 0.30 | ±0.58 |
| F. U.S. Special Forces (SF) 11° C., 91%) | | 1441 | 7 | 0.29 ± 0.07 | 0.06 ± 0.29 | ±0.56 |
| G. USMC Iraq (42° C., 11%) | | 225 | 8 | 0.23 ± 0.08 | −0.05 ± 0.24 | ±0.48 |
| H. USMC Afghanistan (20° C., 20%) | | 586 | 8 | 0.32 ± 0.14 | −0.07 ± 0.34 | ±0.66 |
| I.1. Austral. Sol. (MOPP II) (18° C., 75%) | | 297 | 8 | 0.26 ± 0.07 | 0.03 ± 0.27 | ±0.53 |
| I.2. Austral. Sol. (MOPP IV) (18° C., 72%) | | 244 | 8 | 0.42 ± 0.14† | −0.28 ± 0.34† | ±0.67† |
| Overall* | | | | 0.30 ± 0.13 | −0.03 ± 0.32 | ±0.63 |

Values are mean ± SD.
†Significant difference at p < 0.05.
PPE = Personal Protective Equipment.
Bolded results indicate Bias and where limits of agreement thresholds have been exceeded.
USMC = U.S. Marine Corps.
*Overall RMSE weighted by study duration & n.
Overall bias and limits of agreement computed from all data points.

B. Extended Kalman Filter Model Development

An extended Kalman filter model is comprised of two relationships: a time update model and an observation model. In the estimation of core body temperature the time update model relates how core body temperature changes from time step to time step along with the uncertainty/noise of this change. The observation model relates an observation of heart rate to a core body temperature value along with the uncertainty of this mapping. The time update and observation models are shown in Equations 7 and 8 as regression models with the uncertainty/noise represented as zero mean Gaussian distributions with variances of $\gamma^2$ and $\sigma^2$.

The time update model was defined as a linear regression equation as follows:

$$CT_t = a_1 CT_{t-1} + a_0 + f \text{ where: } f \sim N(0, \gamma) \quad (1)$$

where CT=core temperature, subscript t=time point, $a_1$=time update model coefficient, $a_0$=time update model intercept, f=noise drawn from a Gaussian distribution (N) with mean 0 and standard deviation (SD) $\gamma$. Parameters $a_1$ and $a_0$ were found by least squares regression of $CT_t$ by $CT_{t-1}$. The parameter $\gamma$ was derived from the standard deviation of the discrete probability distribution of $\Delta CT$ points from the development data.

The observation model was defined as a quadratic regression model as follows:

$$HR_t = b_2 CT_t^2 + b_1 CT_t + b_0 + g \text{ Where: } g \sim N(0, \sigma) \quad (2)$$

where $b_2$=observation model quadratic coefficient, $b_1$=observation model coefficient, $b_0$=observation model intercept, g=noise drawn from a Gaussian distribution with mean 0 and SD $\sigma$. Equation 2 shows a quadratic regression model as this was found to fit the development data necessitating the use of the extended Kalman filter. Parameters $b_0$, $b_1$, and $b_2$ were found by quadratic least squares regression fit to eight pairs of core body temperature—heart rate points found by searching for the optimal core body temperature estimation performance of a previous Kalman filter model (Buller et al 2010). The parameter $\sigma$ was found by computing the mean and standard deviation of heart rate values binned by core body temperature at 0.1° C. intervals and taking the mean of the standard deviation values for each bin.

If the model parameters ($a_0$, $a_1$, $\gamma$, $b_0$, $b_1$, $b_2$, and $\sigma$) can be found, a standard set of extended Kalman filter equations can be used to iteratively compute the most likely core body temperature given a series of heart rate observations (see Equations 3-8 discussed above). The simplified equations 3-8 are shown using the model parameters from equations 1 and 2, and where the learned model parameters have been substituted. Thus, given any series of one minute heart rate observations these equations can be used to iteratively compute a series of minute by minute core body temperature estimates. However, at each time step the extended Kalman filter equations can be thought of as operating in the following way: (1) compute an estimate of the current core body temperature using the time update model (see Equation 3), (2) compute the uncertainty of the current core body temperature estimate using the time update model uncertainty (see Equation 4), (3) adjust the current core body temperature estimate using the current observation of heart rate and the observation model weighted by the uncertainty of the observation versus the uncertainty of the current core body temperature estimate (see Equation 7), and (4) adjust the core body temperature estimate uncertainty based upon the uncertainty of the observation (see Equation 8).

The prior Kalman filter model (Buller et al 2010) was used to search for the optimal CT-HR points using our developmental data. The prior Kalman filter linear observation model was split into 7 line segments at eight core body temperature values of 36.5°, 37.0°, 37.5°, 38.0°, 38.5°, 39.0°, 39.5°, and 40.0° C. That Kalman filter model was modified to be run in a piecewise fashion using these seven line segments. For each core body temperature (listed above)

starting with the lowest, the heart rate value (±50 beats/minute in 1 beat intervals) were systemically varied to redefine the Kalman filter observation model at this point. For each heart rate, the redefined Kalman filter model was used to provide estimates of core body temperature given our development data. The heart rate that provided core body temperature estimates with the minimum root mean square error (RMSE) compared to the observed development data was selected. The next highest core body temperature line segment point was then selected and the process repeated. In this way the eight CT-HR pairs were modified by the developmental data from the earlier observation model to a new model that better defined the relationship between core body temperature and heart rate. A quadratic least-squares regression was fit to these points to become the optimized observation model.

C. Model Validation (Statistical Analysis)

The limits of agreement (LoA) method (Bland and Altman 1986) was selected as the most appropriate means for assessing agreement between the observed core body temperature and Kalman filter model estimate. This method plots the average of observed and estimated values against the difference (estimate-observation). Bias is computed as the mean of the differences. Limits of agreement are computed as bias±1.96×standard deviation (SD) of the differences. The limits of agreement provide a range of error within which 95% of all estimates using the extended Kalman filter approach should fall assuming a normal distribution. The initial observed core body temperature values for each study were used as starting values for the extended Kalman filter model and the initial variance was set to zero indicating high confidence in these values. The extended Kalman Filter model was developed using data with one minute intervals. Where data had sampling rates more frequent than the one minute intervals the mean of all values occurring in that minute was used. Where the sampling rate was greater than one minute, values were linearly interpolated.

The Bland and Altman method specifies no a priori limits on what forms an acceptable bias or range of the limits of agreement; instead they suggest these values depend on the measure and its intended use. For this analysis, the model's performance was compared to how the accepted laboratory measures of rectal and esophageal temperatures compare. Bias limits were set to the individual biological variation of ±0.25° C. found by Consolazio, Johnson and Pecora (1963). To set limits of agreement, the literature for comparisons of rectal to esophageal temperatures was examined. Table 3 shows results of bias±SD and limits of agreement for five studies. Taking a weighted mean of all studies suggests that 95% of comparisons of rectal versus esophageal core body temperatures fall within ±0.58° C. This limits of agreement appears to reflect the difficulty in obtaining tight agreement in different methods of core body temperature measurement. This difficulty is highlighted when both esophageal and rectal temperature methods are compared to pulmonary arterial blood temperature where limits of agreement are ±0.59° C. and ±0.78° C. respectively (Lefrant et al 2003).

Table 3 shows the bias and the limits of agreement for studies comparing rectal and esophageal measure of core body temperature.

TABLE 3

| Citation | Bias ± SD | limits of agreement (1.96 * SD) | N |
| --- | --- | --- | --- |
| Kolka* | −0.21 ± 0.17 | ±0.33 | 4 |
| Lee* | −0.35 ± 0.20 | ±0.40 | 7 |

TABLE 3-continued

| Citation | Bias ± SD | limits of agreement (1.96 * SD) | N |
| --- | --- | --- | --- |
| Teunissen et al 2011 | 0.01 ± 0.32 | ±0.63 | 10 |
| Brauer et al 1997 | −0.03 ± 0.42 | ±0.82 | 60 |
| Al-Mukhaizeem et al 2004 | 0.05 ± 0.22† | ±0.43† | 80 |
| | Weighted Mean | ±0.58 | 161 |

*In Byrne and Lim (2007).

†Weighted mean of 3 periods in Table 1, Al-Mukhaizeem et al (2004).

The root mean square error (RMSE) for each individual volunteer and the mean RMSE±SD for each condition were computed. A single factor (study condition) analysis of variance (ANOVA) was used to test for differences in Kalman filter model performance (RMSE, bias, and limit of agreement (LoA)) across conditions in study A and across field studies E through I. To readily identify what factors were causing main effect differences, the least significant difference (LSD) post-hoc test was used. T-tests were used to examine differences in performance between laboratory baseline measures and dehydration, acclimation and clothing configurations studies B, C and D respectively. An overall RMSE was computed, weighted by each individual and study duration. Overall bias and limits of agreement were computed from all data points. Grubbs (1969) outlier detection test was used to identify RMSE and bias measures that differed significantly from each study's group responses.

D. Model Development

FIG. 5A shows the discrete probability distribution of ΔCT used for the time update model and FIG. 5B shows a scatter plot of all core body temperature by heart rate points showing the mean HR±SD for core body temperature binned by 0.1° C. intervals. The discrete probability distribution mean was found to be 0.001°±0.022° C./minute. The regression of previous core body temperature with current was found to be $CT_t = 0.9984 \cdot CT_{t-1} + 0.0622$ with an $r^2 = 0.99$. With the mean of the discrete probability distribution close to zero, and the regression coefficient close to one, and because it was expected to be equally likely that core body temperature will either increase or decrease we set our time update model to $a_1 = 1$, $a_0 = 0$ and $\gamma = 0.022$.

The optimal piecewise line segment points that provided the best RMSE (0.27°±0.10° C.) and largest number of points within ±0.58° C. (96.1±6.7%) are shown in FIG. 5B. A quadratic fit to these points defines the observation mapping function as $b_0 = -7887.1$, $b_1 = 384.4286$, and $b_2 = -4.5714$. The mean standard deviation for the binned heart rate=18.88±3.78 beats/minute so σ is set to 18.88. To keep the extended Kalman filter model simple the positively (low CT) and negatively (high CT) skewed heart rate distributions at the extremes of core body temperature are ignored. Keeping the assumption that heart rate is normally distributed across all core body temperatures has the effect of slightly under and over estimating the rate of rise of core body temperature for low and high core body temperatures respectively.

Table 4 shows the iterative application of these equations to a series of heart rate observations given a starting $CT_0 = 37.94°$ C. and a starting variance of $v_0 = 0$.

TABLE 4

| heart rate | t | $\hat{CT}_t$ (eq. 3) | $\hat{v}_t$ (eq. 4) | $c_t$ (eq. 5) | $k_t$ (eq. 6) | $CT_t$ (eq. 7) | $v_t$ (eq. 8) |
|---|---|---|---|---|---|---|---|
|  | 0 |  |  |  |  | 37.94 | 0 |
| 124 | 1 | 37.94000 | 0.00048 | 37.55077 | 0.00005 | 37.94031 | 0.00048 |
| 111 | 2 | 37.94031 | 0.00097 | 37.54791 | 0.00010 | 37.93962 | 0.00096 |
| 119 | 3 | 37.93962 | 0.00145 | 37.55427 | 0.00015 | 37.93979 | 0.00144 |
| 145 | 4 | 37.93979 | 0.00192 | 37.55266 | 0.00020 | 37.94525 | 0.00191 |

Bold font = observed or initialization data. Equations 3-8 are applied iteratively to compute $CT_t$ and $v_t$.

Figures 6A, 6B, 6C:
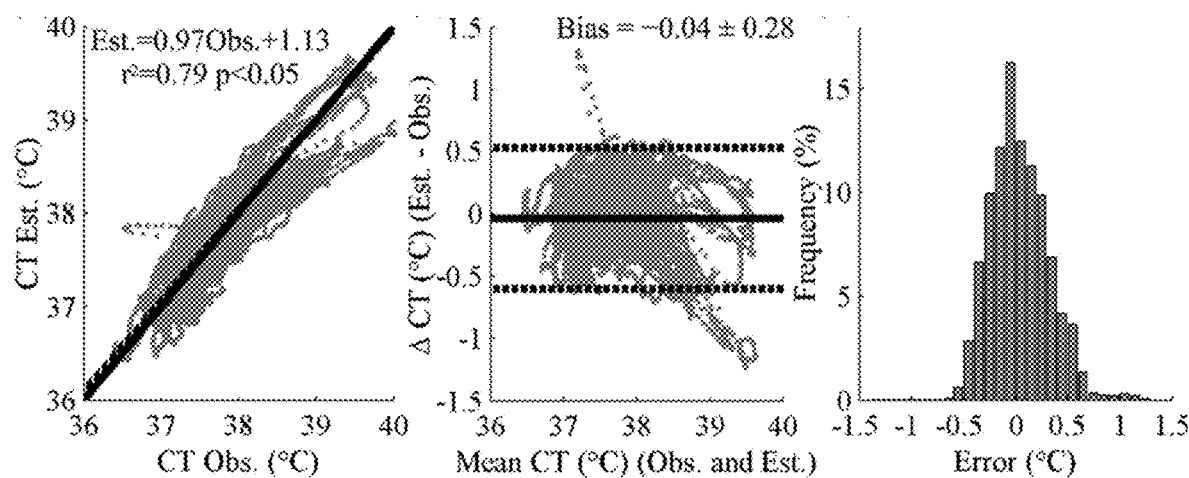
FIG. 6A shows a scatter plot of observed (Obs.) core body temperature (CT) versus estimated (Est.) core body temperature for the development data, showing the line of identity (solid) and least squares regression line (dashed).
FIG. 6B shows a Bland Altman plot showing bias (solid) and ±1.96 SD (dashed) for the development data.
FIG. 6C shows a normalized histogram of model error for all training data.

FIGS. 6A and 6B illustrate the performance of the learned model on the development data. FIG. 6A shows a scatter plot of estimated core body temperature by observed core body temperature (CT), the line of identity and a least squares linear regression fit to the development data. The scatter plot of observed (Obs.) core body temperature versus estimated (Est.) core body temperature for the development data, showing the line of identity (solid) and least squares regression line (dashed). FIG. 6B shows a Bland Altman Plot of mean of observed and estimated core body temperature versus estimated-observed core body temperature (CT). The bias=−0.04°±0.28° C. with the LoA=±0.55° C. The Bland Altman plot showing bias (solid) and ±1.96 SD (dashed) for the development data. FIG. 6C shows a normalized histogram of the model error.

E. Model Validation

Figures 7A, 7B, 7C:
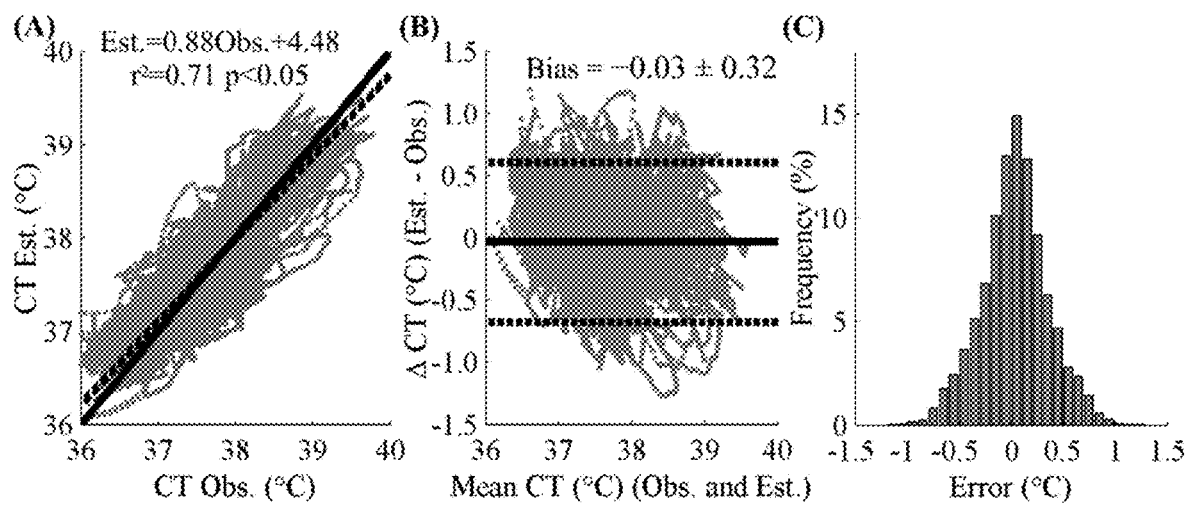
FIG. 7A shows a scatter plot of observed (Obs.) core body temperature (CT) versus estimated (Est.) core body temperature for the validation data, showing the line of identity (solid) and least squares regression line (dashed).
FIG. 7B shows a Bland Altman plot showing bias (solid) and ±1.96 SD (dashed) for the validation data.
FIG. 7C shows a normalized histogram of model error for all validation data.

The extended Kalman filter model using Equations 3-8 was validated against 150 individual test sessions with 83 different volunteers (providing more than 52,000 core body temperature observations) and had an overall bias of −0.03°±0.32° C. with the LoA=±0.63° C. The overall weighted mean RMSE was 0.30°±0.13° C. FIG. 7A shows a scatter plot of estimated core body temperature by observed core body temperature, the line of identity and a least squares linear regression fit to the validation data. The scatter plot of observed (Obs.) core body temperature versus estimated (Est.) core body temperature for the validation data, showing the line of identity (solid) and least squares regression line (dashed). FIG. 7B shows a Bland Altman Plot of mean of observed and estimated core body temperature versus estimated-observed core body temperature of the validation data. The Bland Altman plot showing bias (solid) and ±1.96 SD (dashed) for validation data. FIG. 7C shows a normalized histogram of the model error for all the validation data.

Table 2 (see above) presents the mean RMSE, bias, and limits of agreement (*LoA*) for estimated versus observed core body temperature for the laboratory and field validation studies. FIGS. 8A1-8A18 show individual Bland-Altman plots showing bias (solid lines) and ±1.96 SD (dashed lines) for each study including individual conditions. FIGS. 8B1-8B18 show the mean observed and estimated core body temperature plots for all the studies including conditions to provide more detailed overview of the model performance.

At environmental conditions 35° C., 30% relative humidity, and an EE rate of 350 W (study A.4), the bias exceeded our acceptability threshold and is significantly more negative than the study conditions A.3, A.5, and A.6 (F=2.77, P<0.03). The hydrated baseline condition (B.1) exceeded both the bias and limits of agreement criteria, and is significantly different from the dehydrated condition (B.2) on the measures of RMSE and limits of agreement (t=2.21, P<0.05; and t=3.05, P<0.01 respectively). For the field studies mild conditions (18° C.) with high EE rate (about 685 W) and encapsulation in PPE (1.2) has significantly greater RMSE, and negative bias (F=4.24, P<0.004, F=3.78, P<0.007, respectively) than the other filed studies (E, F, G, H, and I.1); and significantly greater limits of agreement than studies G and I.1 (F=2.68 and P<0.03, respectively).

Table 5 presents four individuals identified as outliers using the Grubbs criterion test from seven of the studies. No individual characteristic stands out as a factor in determining the outliers. Individuals with RMSE and/or bias identified as outliers from 2-tailed Grubbs test.

TABLE 5

| Individual (age, ht, wt., % fat) | Study | Outlying RMSE (° C.) | Outlying Bias (° C.) |
|---|---|---|---|
| 23, 1.70 m, 69 kg | A.2, A.3, A.4 | 0.60†, 0.58, 0.74‡ | −0.59†, −0.55†, −0.72 |
| *, 1.73 m, 72 kg, 9% | C.2 | 0.48‡ | −0.39 |
| 38, 1.86 m, 98 kg, 28% | D.1, D.2 | 0.38, 0.54 | 0.29†, 0.50‡ |
| 22, 1.85 m, 88 kg, 15% | H | 0.60‡ | −0.55† |

*Individual age not available.
†p < 0.05.
‡Approaching significance.

Table 6 summarizes the performance of the extended Kalman filter model across a range of temperatures and TEE rates with clothing configurations from shorts and t-shirts to partial encapsulation. The extended Kalman filter model performance for a variety of temperatures and energy expenditure rates with acclimated, hydrated volunteers, not encapsulated in personal protective equipment.

TABLE 6

|  |  | Environmental Temperature (° C.) | | | | |
|---|---|---|---|---|---|---|
|  |  | 9 to 13 | 18 to 20 | 24 to 27 | 33 to 35 | 40 to 45 |
| Energy Expenditure Rate | Low (<=375 W) | ? | ?↑ | ? | − | ?↑ |
|  | Moderate (376-525 W) |  | ?↑ | ?↑ | ? |  |
|  | High (526-675 W) |  | ? | ? | ? | ? |
|  | Very High (>675 W) |  |  |  | +↑ |  |

? = bias is <±0.13,
†limits of agreement exceeds ±0.58 by less than 0.1° C.,
↑limits of agreement exceeds ±0.58 by more than 0.1° C.,
−underestimation of CT,
+overestimation of CT,
white area = no data.

F. Discussion

This section discusses the extended Kalman filter model as embodied in the simplified Equations 3-8 discussed above.

The extended Kalman filter model has an overall bias of only −0.03°±0.32° C. and limits of agreement of ±0.63° C. indicating that 95% of all model estimates fell within this range of the observed core body temperature. The model has a similar limits of agreement to those found when comparing rectal and esophageal measurements of core body temperature (±0.58° C., see Table 3) and is within the limits of agreement for rectal and esophageal measures found by Teunissen et al (2011) and Brauer et al (1997) of ±0.63° C. and ±0.82° C., respectively.

Using the aggregated results of the various studies, with clothing configurations from shorts and t-shirts to partial chemical biological encapsulation; it is possible to examine the performance of the model across a large temperature range for several different rates of energy expenditure. Table 6 above summarizes the performance of the model in terms of our comparison criteria. For most temperatures and work rates, the model provides core body temperature estimates with a bias and limits of agreement that are similar to those found in comparisons of rectal versus esophageal temperatures. However, at temperatures of 33° to 35° C. there are two exceptions. First, at low work rates the model significantly underestimates core body temperature, and second at very high work rates the model significantly overestimates core body temperature. These errors can be tolerated in the context of using the model for maintaining the safety of individuals. At low work rates the underestimation poses limited risk for missing individuals under thermal strain. In fact, the core body temperature observations for this eight hour series of work rest cycles (study A.4) never exceeded 38.5° C. as depicted in FIG. 8B4. Conversely, at very high work rates the model tends to err on the side of false positives rather than missing thermally stressed individuals.

Analysis of the laboratory studies also demonstrates that the model provides core body temperature estimates with small bias and limits of agreement within or close to our comparison threshold when volunteers are dehydrated, encapsulated in chemical biological PPE, or in an unacclimated state.

Only one set of conditions proved difficult for using the model in a safety assessment context. The model performs significantly less-well estimating core body temperature of individuals engaged in very strenuous activity, in cooler temperatures while encapsulated in chemical biological PPE (MOPP IV) (study I.2). This particular study examined volunteers on a 5 km road march conducted at a 15 minute/mile pace in full chemical biological protective garments. Here the model clearly does not account for the full rise in core body temperature seen during the road march (see FIG. 8B18, panel I.2) and hence has a large negative core body temperature bias. Although the work rate and clothing vapor occlusiveness are similar to that in the clothing laboratory study (study C), the ambient temperature was cooler (18° C. versus 35° C.). Under these conditions it appears that the thermoregulatory response of the volunteers was to widen the CT-to-skin temperature gradient, by allowing core body temperature to rise, rather than increase skin blood flow (see Sawka and Young 2006). Thus, the observed rise in core body temperature was greater than the rise the model would estimate from heart rate. Under the warmer conditions of the clothing laboratory study (study C) the model performed adequately.

When compared to the other recent approaches at providing non-invasive estimates of core body temperature the model performs well. The model estimates of core body temperature have a similar bias when compared to the heat flux sensor proposed by Gunga et al (2008). However, limits of agreement for the heat flux sensor in environmental conditions of 25° C. and 40° C. were much higher (±0.71° C. and ±0.74° C., respectively) than all our conditions except study B.1. Similarly, when the model is directly compared to a real time implementation of a physics based thermoregulatory model (Yokota et al 2008) across study conditions A.1-A.5 (bias±LoA: −0.24±0.67; −0.25±0.66; −0.08±0.77; −0.23±0.65; 0.10±1.09° C., respectively) (De-Groot et al personal communication) the model performs better with a bias closer to zero in four out of the five conditions and has limits of agreement less than those provided by the thermoregulatory model.

As with any method there is a distribution in performance (see FIGS. 6A-6C) where the model will more accurately estimate core body temperature in some individuals than others. The overall and individual study Bland Altman charts in combination with the outlier analysis show that the model predicts core body temperature very well except for a small number of individuals. The outlier analysis (see Table 5) identified four individuals where the model did not perform as well as the group. This same number is predicted by the limits of agreement methodology (5% of 83) where 5% of the population would be expected to fall outside of the ±0.63° C. limits of agreement bounds. For the outlier from study A.2, A.3, and A.4 the error is systematically negative. Similarly, the individual identified as an outlier in D.1 and D.2 has a systematic positive bias in core body temperature estimations. With these outliers performance of the model appears to be individual specific rather than condition specific, and so systematic biases for individuals appear to be correctable. The model parameters do allow for individualization by both age and fitness.

Other factors can affect heart rate, and thus the core body temperature estimation, include diet, caffeine, sleep, and psychological stress. The effects of diet and caffeine on heart rate will likely be outweighed by activity and thermoregulation. There were no controls for these factors in the field studies. Since it is likely that many volunteers were taking caffeinated products, the performance of the model includes the potential influence of caffeine. During sleep heart rate is reduced to low levels, but the model's estimation of core body temperature appears appropriate in these situations given the sleep data at the mid-point of study F. However, the impact of elevated heart rate from sustained psychological stress on the model's performance is unknown.

Although in some conditions the model provides limits of agreement that exceed our comparison threshold, it is important to highlight both the simplicity of the present model and that the limits of agreement calculations include all data with heart rate transients from the start and end of exercise. These transient periods are included to demonstrate that the model can track core body temperature during dynamic real-world periods of work and rest. Teunissen et al 2011 examined the limits of agreement between rectal and esophageal core body temperature across periods of rest, exercise and recovery and found similar limits of agreement of ±0.63° C. The model in at least one embodiment uses only one variable, heart rate, to estimate core body temperature with no adjustment for height, weight, body composition, fitness, or age.

Finally, while the model is not a replacement for the direct measurement of core body temperature the findings suggest the model is accurate, precise and practical enough to provide an indication of thermal work strain for use in the work place. Using an estimate of core body temperature in conjunction with heart rate to obtain a physiological strain index (PSI) value would provide a simple mechanism for alerting workers to possible excessive thermal work strain.

Update to ECTEMP™

This disclosure shows that by the addition of two additional sensors and individualization how changes to the "observation" model based upon physiological insight and adjustments to the "time-update" model provide a general method for estimating core body temperature for the general population.

"Observation" Model Update

The original quadratic equation used for the extended ECTemp™ Kalman filter "observation" model (and discussed above) incorrectly estimates core body temperature at lower and higher heart rates. For example, the quadratic equation estimates that heart rate decreases as temperature increases above 41° C. In addition, the quadratic equation does not predict core body temperature under 36° C. unless heart rate drops below physiological limits (<27 bpm).

A sigmoid shaped curve is required to correctly represent the relationship between heart rate and core body temperature. Physiologically humans have a resting heart rate and a maximal heart rate which represents an individual's heart rate range. When resting/sleeping heart rate and core temperature data are added to the original ECTemp™ training data the appropriateness of the sigmoid shaped relationship can be seen quite clearly (see FIG. 2 taken from Looney et al. 2018).

Several important points need to be made about the selection and fit of the function of the "observation model". First, a sigmoid shaped curve explains the full range of core temperatures from rest through high intensity work. Linear, polynomials, and exponential functions fail to describe the relationship between core body temperature and heart rate. Second, the curve cannot be fit using the classic sigmoid function which approaches both asymptotes symmetrically. The asymmetrical physiological relationship between core body temperature and heart rate can be seen in FIGS. 10A and 10B. Third, the function is not fit by direct regression methods or other statistical approaches. Instead the bounds are set on the insight that the lower limits of the relationship should be at the lower limits of the data distribution and the higher limits are set by the higher limits of the data distribution. This approach is novel and again based on physiological insight. All other approaches in the literature use direct statistical approaches to fit the model.

The extended Kalman filter "Observation" model can then be written as a generalized logistic function (Richards, 1959):

$$HR_t = A + \frac{K - A}{\left(1 + Qe^{-B(\hat{C}T_t - M)}\right)^{1/v}} \quad (9)$$

where A=lower asymptote, K=upper asymptote, Q=is the value when estimated core temperature ($\hat{C}T_t$) equals M, B=the growth rate, M=sets the starting core temperature ($\hat{C}T_t$) value, and v=affects the asymptote where maximum growth occurs. One fit of the curve sets a minimum heart rate as 41 beats per minute, a maximum heart rate as 193, and a mid-point core temperature of 37.84° C., and has superior accuracy compared to the quadratic ECTemp equation (equation 10).

$$HR_t = 41 + \frac{152}{\left(1 + 0.06e^{-0.89(\hat{C}T_t - 37.84)}\right)^{1/0.07}} \quad (10)$$

For the extended Kalman filter the gradient is calculated as (equation 11):

$$m_t = \frac{(8.1168e^{-0.89(CT - 37.84)} + 1)^{-15.2857}}{0.07} \quad (11)$$

The generalized logistic function is necessary to enable the easy adjustment of the "observation" model for a number of parameters (age, fitness, passive heating and cooling, environmental conditions, clothing). The "observation model" now includes seven model parameters that can be set for specific individuals, activities, and environments. This includes critical values such as minimum and maximum core temperatures.

Age Adjustments

Maximal heart rate decreases with age. For example, a rule of thumb is that a maximum heart rate=220−age. Physiologically based representations of the observation model can be adjusted to account for age or different heart rate maxima and minima. These age and fitness heart rate maxima and minima can be readily translated into the general logistic equation by altering the lower and upper asymptote values (A and K from equation 9).

Passive Heating/Cooling Adjustments

Theoretically the "observation" model represents the underlying physiological assumption of a fixed ratio of cardiac output for work and skin blood perfusion. The original work and subsequent validation show that this ratio holds fairly constant for different exercise intensities in temperate to very hot conditions (45° C.), and for different clothing ensembles from shorts and t-shirts to full encapsulation in personal protective equipment. This underlying assumption, however, can vary. One would expect from passive heating that the algorithm would underestimate the rise in core temperature as there is no heat generating information contained in the heart rate. Seo et al. (2016) in their validation of the algorithm implemented in a commercial physiological status monitoring device found acceptable performance for treadmill and cycle exercise, but that the algorithm systematic underestimated Tc through passive heating. Similarly, with exercise in cold environments, limited blood flow to the skin would be needed for cooling and hence the algorithm would overestimate core body temperature in this situation (Delves et al. 2016). When the "observation" model is represented as a sigmoid, this line can be modified to represent a change in the underlying ratio of cardiac output for exercise versus heat transfer. These adjustments would be made by adjusting the M and v parameters in the standard logistic model (equation 9).

In an embodiment these passive heating/cooling adjustments to the "observation" model would be made based upon an environmental temperature sensor or skin temperature sensor. With passive heating, skin temperature would exceed the core body temperature. Similarly, with very cool environments, skin temperature would be expected to be below normal levels for a given activity.

"Time-Update" Model Adjustments

Fitness Adjustments

While to some extent fitness can be accounted for by the changes in heart rate maxima and minima, another adjustment is made in the other Kalman filter model—the "time-update" model. An individual with greater cardiovascular fitness has greater potential cardiac output and thus for a given heart rate is able to both generate more work and thereby heat and provide more blood flow for cooling. Thus a fitter individual can change core body temperature at a faster rate compared to someone who is less fit. The KF model was developed, tuned and validated from volunteers with fairly homogenous fitness. As fitness levels deviate from the training data it would be expected that the model's performance would degrade. However, one of the model parameters described herein can be modified to account for fitness. To test this hypothesis a new variance ($\gamma$ see equation 1) for the $\Delta$Tcore time-update model (see FIG. 5A) was learned from the Elite distance runner development data (Ely et al. 2009) then tested on the remaining hold-out elite distance runner data (n=12). FIGS. 4A1 and 4B1 show the regular ECTemp $\gamma$=0.024 that underestimates core temperature for elite athletes (FIG. 4A1) and the updated $\gamma$=0.043 that accurately estimates core body temperature (FIG. 4B1).

Similarly, for less fit individuals the variance for $\gamma$ can be reduced to less than 0.024 to account for their inability to provide both fuel and oxygen to muscles for work and blood to the skin for cooling.

Exercise/Recovery Adjustments

In different circumstances it can be hypothesized that there could be a difference in the rate of change in core body temperature between increase in core temperature during exercise and the decrease of core temperature during recovery. This can simply be accounted for by changing the gamma ($\gamma$) value in the "time-update" model based upon whether an individual is exercising or recovering from exercise. In an embodied form an accelerometer could be used to identify periods of exercise/work from periods of rest. Based upon accelerometry $\gamma$ values will be changed to affect the rate of core temperature rise or fall. This change can additionally be implemented in a switching state extended Kalman filter framework.

Study Design

This investigation used a conventional validation approach to the development and validation of a new sigmoid equation for ECTemp™. The present investigation aimed to improve resting CT estimation by retraining a new sigmoid equation for ECTemp™ on an updated development dataset. The original development dataset was from an investigation (Tharion et al., 2013) that evaluated the use of a physiological status monitoring system by soldiers during considerable thermal-work strain in the field. The updated development dataset combines the original development dataset (Tharion et al., 2013) with resting CT data from half of the volunteers randomly selected from a supplementary dataset (Welles et al., 2018). The remaining volunteers from the supplementary dataset were used in the model validation dataset. We took this approach to fit a new sigmoid equation that would correct lower CT estimates while producing higher CT estimates that are nearly identical to the original quadratic equation. All volunteers were briefed on the procedures, benefits, and risks of the study and gave their informed consent prior to data collection. The investigators adhered to the policies for protection of human subjects as prescribed in Army Regulation 70-25. All research was conducted under the oversight of Institutional Review Boards.

Model Development

The updated model development dataset included data from 25 volunteers (age, 23±3 yrs; height, 1.72±0.07 m; body mass, 68.5±8.1 kg). The sample included three women (age, 24±4 yrs; height, 1.70±0.02 m; body mass, 63.3±7.3 kg) and 11 men (age, 22±2 yrs; height, 1.75±0.07 m; body mass, 70.9±7.9 kg). The sample included the 17 male U.S. Army soldiers (age, 23±4 yrs; height, 1.79±0.08 m; body mass, 81.3±10.8 kg) from the original development dataset (Tharion et al., 2013). Heart rate (Equivital EQ02, Hidalgo Cambridge, UK) and CT (Jonah Thermometer Pill, Respironics, Bend, OR) data were collected during a summer field training exercise at Fort Bragg, North Carolina (air temperature, 24-36° C.; relative humidity (RH), 42-97%; wind speed, 0-4 ms$^{-1}$). The field exercise included periods of sleep, rest, foot movement, and vigorous upper body work resulting in a wide range of CT (36-40° C.).

The eight volunteers from the supplementary dataset (Welles et al., 2018) that were randomly assigned to the model development dataset (age, 22±3 yrs; height, 1.74±0.07 m; body mass, 68.8±9.1 kg) included three women (age, 24±4 yrs; height, 1.70±0.02 m; body mass, 63.3±7.3 kg) and five men (age, 21±1 yrs; height, 1.76±0.08 m; body mass, 72.2±8.4 kg). Heart rate (Equivital EQ02, Hidalgo Cambridge, UK) and CT (Jonah Thermometer Pill, Respironics, Bend, OR) data were collected over two calorimeter chamber visits. Each volunteer ingested a thermometer pill approximately 2 hr before data collection began. calorimeter chamber temperature was set to each volunteer's preferences between 18-22° C. during pre-trial equipment fitting and was regulated within ±2° C. Volunteers entered into the calorimeter chamber at approximately 1700 hr and were restricted to sleep or sedentary tasks (e.g., computer work, watching television) until ~0930 hr the following day. Volunteers were allowed to consume water ad libitum but food intake was restricted to a standardized dinner (1800 hr) and breakfast (0700 hr).

Model Validation

The eight volunteers from the supplementary dataset (Welles et al., 2018) that were randomly assigned to the model validation dataset (age, 24±3 yrs; height, 1.71±0.07 m; body mass, 68.2±7.1 kg) included 2 women (age, 24±4 yrs; height, 1.62±0.03 m; body mass, 63.4±3.2 kg) and 6 men (age, 24±3 yrs; height, 1.74±0.06 m; body mass, 69.8±7.3 kg). HR and CT data were collected from these volunteers over two calorimeter chamber visits. Each volunteer ingested a thermometer pill approximately 2 hr before data collection began. Calorimeter chamber temperature was set to each volunteer's preferences between 18-22° C. during pre-trial equipment fitting and was regulated within ±2° C. Volunteers entered into the calorimeter chamber at approximately 1700 hr and were restricted to sleep or sedentary tasks (e.g., computer work, watching television) until ~0930 hr the following day. Volunteers were allowed to consume water ad libitum but food intake was restricted to a standardized dinner (1800 hr) and breakfast (0700 hr).

ECTemp™ Algorithm

The ECTemp™ algorithm is based upon an extended Kalman filter (Welch & Bishop, 1995) that is comprised of a time update and observation model. The original development and validation study (Buller et al., 2013) contains a detailed description of how each model coefficient was derived. The time update model relates how CT changes minute-to-minute and the uncertainty associated with this change. The observation model relates an observation of HR to CT as well as the uncertainty of this mapping. The initial CT observed was used to initialize ECTemp™ for all experiments conducted in this investigation. Subsequently, the following six equations are applied iteratively after each minute time point (t) to provide a new estimate of $CT_t$ and its associated variance ($v_t$) given a current HR observation ($HR_t$) as well as the previous CT estimate ($CT_{t-1}$) and previous variance ($v_{t-1}$).

(1) Compute a CT preliminary estimate ($\hat{C}T_t$) based on the previous CT estimate.

$$\hat{C}T_t = CT_{t-1} \tag{12}$$

(2) Compute a preliminary estimate of the variance of the CT estimate ($\hat{v}_t$) based on the previous CT variance ($v_{t-1}$).

$$\hat{v}_t = v_{t-1} + 0.000484 \tag{13}$$

(3) Compute the extended Kalman filter mapping function variance coefficient ($m_t$).

$$m_t = -9.1428\hat{C}T_t + 384.4286 \quad (14)$$

(4) Compute the Kalman gain ($k_t$) weighting factor based on the preliminary estimate of variance and using the extended Kalman filter mapping function variance coefficient ($m_t$).

$$k_t = \frac{\hat{v}_t m_t}{m_t^2 \hat{v}_t + 356.4544} \quad (15)$$

(5) Compute the final CT estimate ($CT_t$) using the preliminary time-update estimate, the error between the $HR_t$ observation and the expected HR given the preliminary estimate of CT.

$$CT_t = \hat{C}T_t + k_t\{HR_t - (-4.5714\hat{C}T_t^2 + 384.4286\hat{C}T_t - 7887.1)\} \quad (16)$$

(6) Compute the variance of the final CT estimate ($v_t$).

$$v_t = (1 - k_t m_t)\hat{v}_t \quad (17)$$

The new sigmoid equation was fit using a generalized logistic function (Richards, 1959). The generalized logistic function used can be written as:

$$HR_t = A + \frac{K - A}{\left(1 + Qe^{-B(\hat{C}T_t - M)}\right)^{1/v}} \quad (9)$$

where A=lower asymptote, K=upper asymptote, Q=is the value when estimated core temperature ($\hat{C}T_t$)=M, B=the growth rate, M=sets the starting $\hat{C}T_t$ value, and v=affects the asymptote where maximum growth occurs.

Statistical Analyses

All statistical analyses were performed using RStudio (Version 0.98.1056, RStudio, Inc., Boston, MA). Data are displayed as mean±standard deviation (SD). All CT data were visually inspected to identify outliers and artifact associated with fluid ingestion. The goal of this investigation was to update Equations 3 and 5. The sigmoid model was fit using a generalized logistic function to minimize the squared error using the iterative techniques previously described in the original development study (Buller et al., 2013). Bias was computed as the mean of the differences between the estimated CT and observed CT. 95% limits of agreement (95% LoA) were computed as bias±1.96·SD.

Results

FIGS. 10A and 10B display HR plotted on CT and the line of best fit for the quadratic model from the original investigation data and the new sigmoid model learned from the development data from the current study. The optimal equation for the sigmoid model was determined to be the following:

$$HR_t = 41 + \frac{152}{\left(1 + 0.06e^{-0.89(\hat{C}T_t - 37.84)}\right)^{1/0.07}} \quad (10)$$

The sigmoid equation was incorporated into the original algorithm by replacing Equations 14 and 16 with Equations 18 and 19 respectively:

$$m = \frac{(8.1168e^{-0.89(CT - 37.84)})(0.06e^{-0.89(CT - 37.84)} + 1)^{-15.2857}}{0.07} \quad (18)$$

$$CT_t = \hat{C}T_t + k_t\left\{HR_t - \left(41 + \frac{152}{\left(1 + 0.06e^{-0.89(\hat{C}T_t - 37.84)}\right)^{1/0.07}}\right)\right\} \quad (19)$$

Figure 11B:
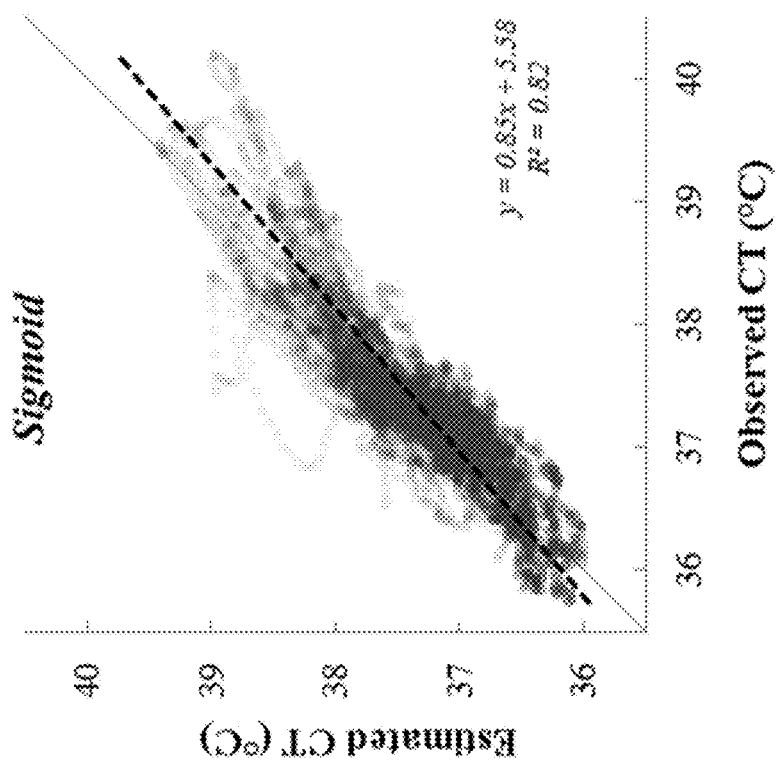
FIGS. 11A and 11B display estimated CT plotted on observed CT from the development data for the quadratic (FIG. 11A) and sigmoid (FIG. 11B) models with linear trendline (dashed).
Figure 11A:
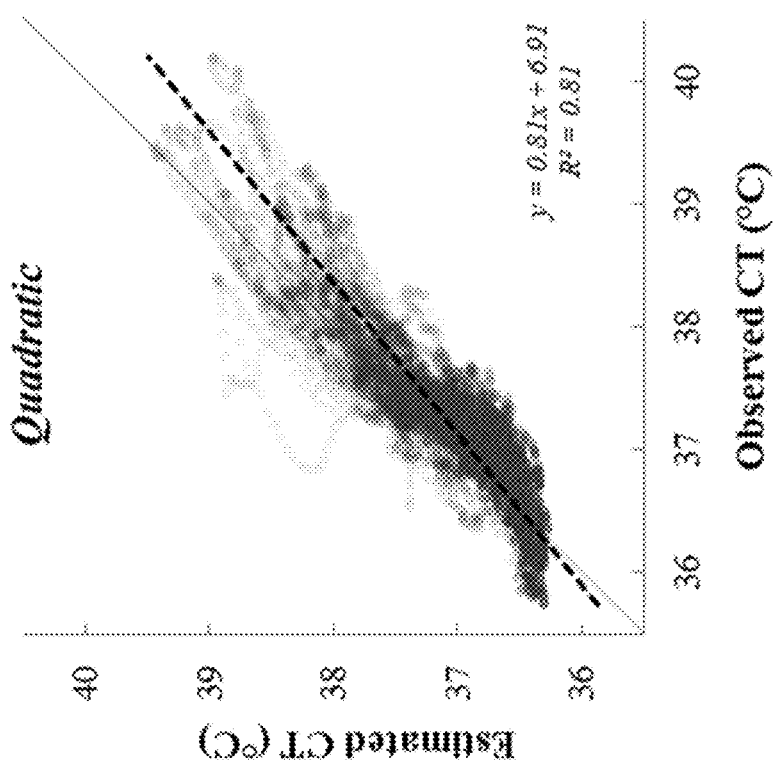
Figure 12A:
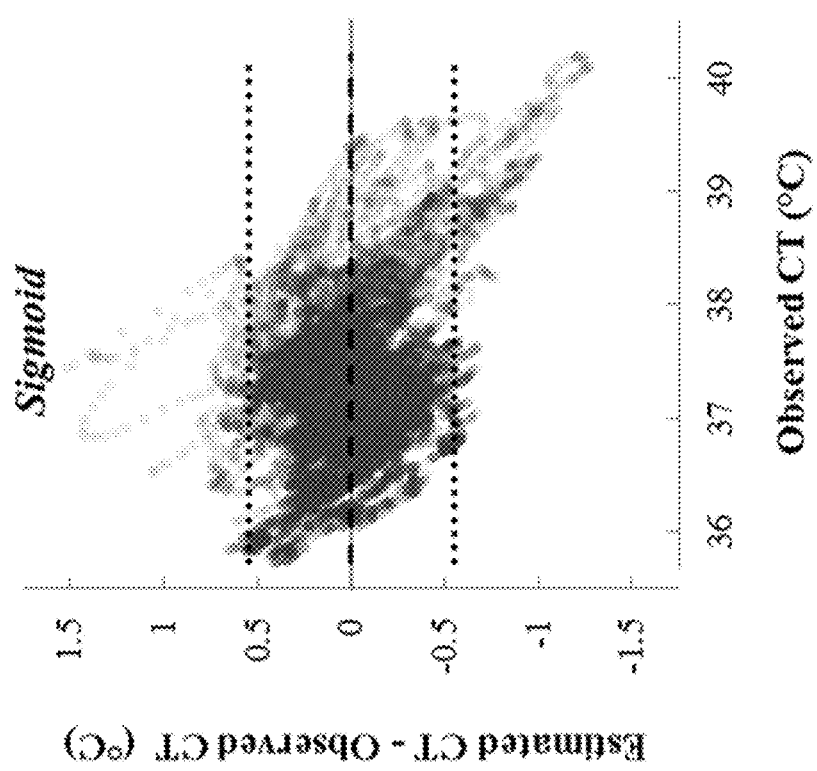
FIGS. 12A and 12B display Bland-Altman plot of agreement between estimated and observed core temperature (CT) from the development data for the quadratic (FIG. 12A) and sigmoid (FIG. 12B) models with bias (dashed line) and lower and upper 95% limits of agreement (dotted lines).
Figure 12B:
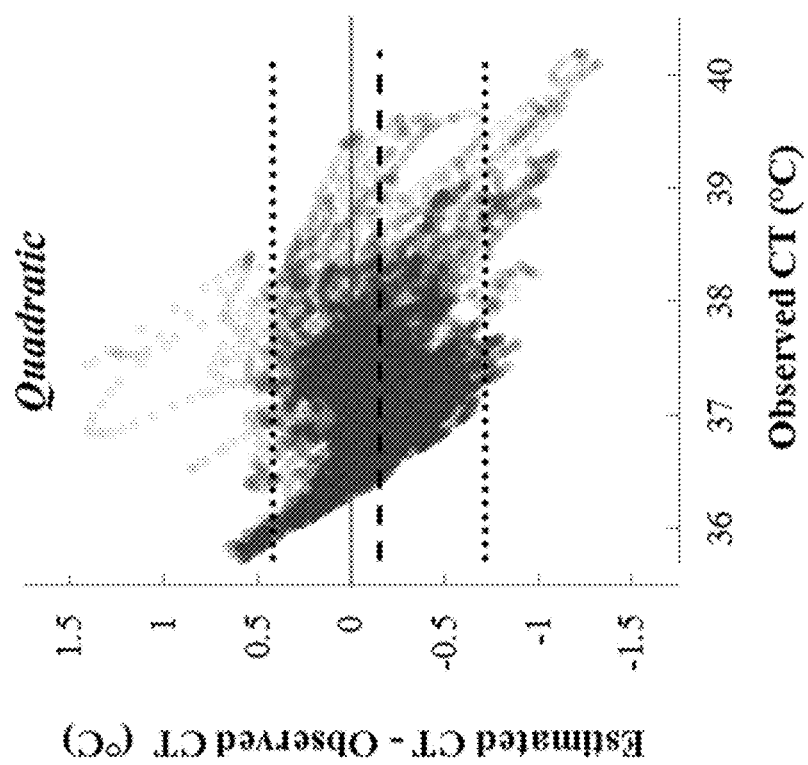

As shown in FIGS. 11A and 11B, the quadratic model (FIG. 11A) had a higher RMSE (0.33° C.) than the sigmoid model (FIG. 11B) (0.28° C.). FIGS. 12A and 12B display Bland-Altman plots from the development data for the quadratic (FIG. 12A) and sigmoid (FIG. 12B) models. Both the bias and 95% LoA were higher for the quadratic model (bias, −0.15±0.29° C.; 95% LoA, [−0.72° C., 0.42° C.]) compared to the sigmoid model (bias, 0.00±0.28° C.; 95% LoA, [−0.55° C., 0.55° C.]).

Figure 13A:
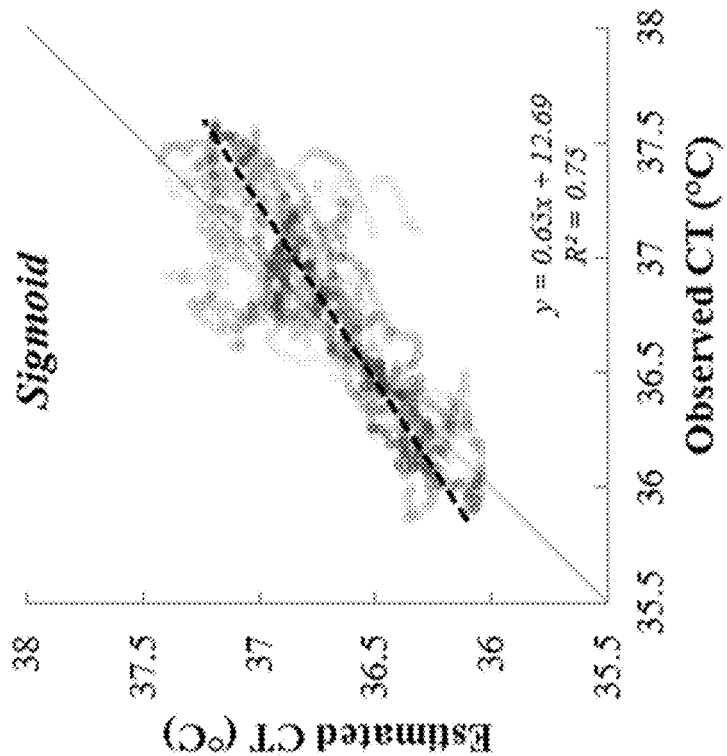
FIGS. 13A and 13B display estimated core temperature (CT) plotted on observed CT from the validation data for the quadratic (FIG. 13A) and sigmoid (FIG. 13B) models with linear trendline (dashed).
Figure 13B:
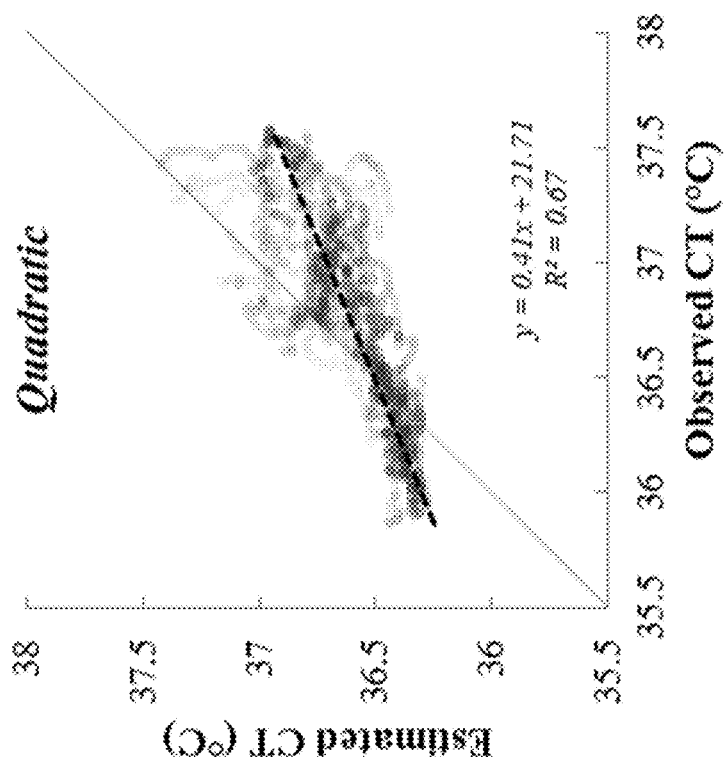
Figure 14B:
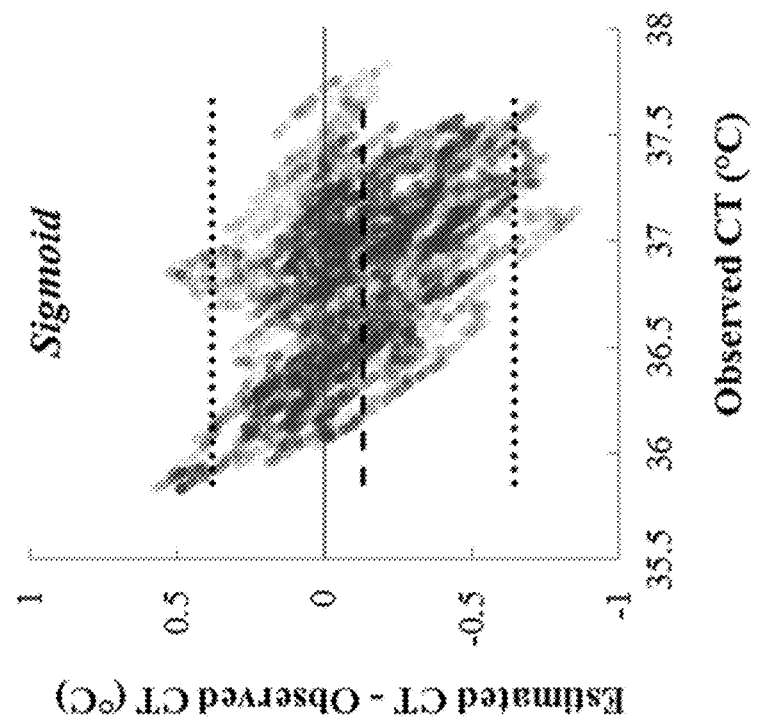
FIGS. 14A and 14B display Bland-Altman plot of agreement between estimated and observed temperature (CT) from the development data for the quadratic (FIG. 14A) and sigmoid (FIG. 14B) models with bias (dashed line) and lower and upper 95% limits of agreement (dotted lines).
Figure 14A:
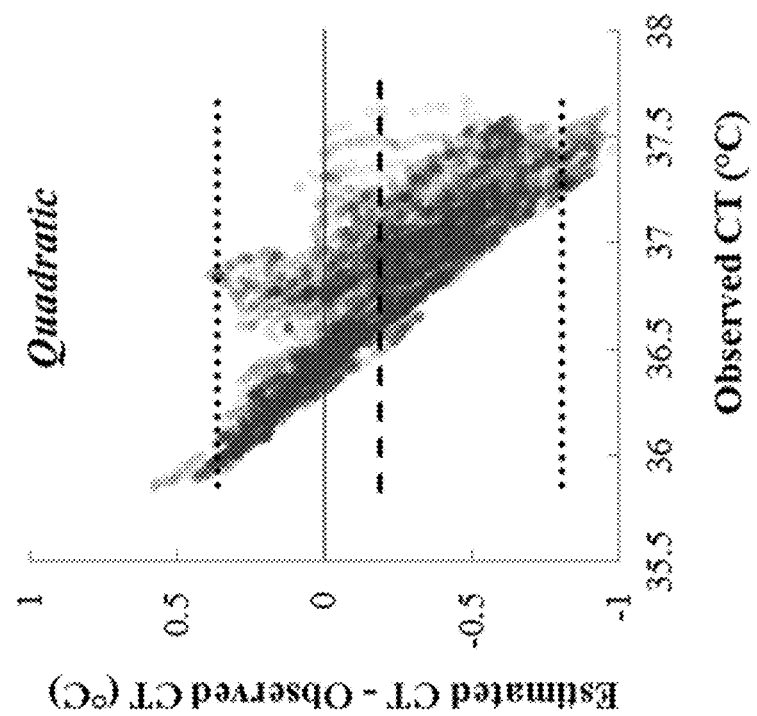

FIGS. 13A and 13B display estimated CT plotted on observed CT from the validation data for the quadratic (FIG. 13A) and sigmoid (FIG. 13B) models. The quadratic model had a higher RMSE (0.37° C.) than the sigmoid model (0.29° C.). FIGS. 14A and 14B display Bland-Altman plots from the validation data for the quadratic (FIG. 14A) and sigmoid (FIG. 14B) models. Both the bias and 95% LoA were higher for the quadratic model (bias, −0.22±0.30° C.; 95% LoA, [−0.81° C., 0.37° C.]) compared to the sigmoid model (bias, −0.13±0.26° C.; 95% LoA, [−0.64° C., 0.38° C.]).

This update demonstrates that the ECTemp™ algorithm closely estimates resting CT. The sigmoid model was superior to the quadratic model in each metric analyzed and is consequently preferable for both resting and active CT estimation. The new sigmoid ECTemp™ is a viable alternative to direct resting CT measurement. Future research needs to evaluate ECTemp™'s circadian rhythm estimation applications.

While this update demonstrated the superior accuracy of the new ECTemp™ model, the sigmoid function is also advantageous since features, such as the range of HR values, can be more easily adjusted than the quadratic function. This added flexibility would allow for individualization of the ECTemp™ model to a person's resting and maximal heart rates similar to the Karvonen formula (Karvonen & Vuorimaa, 1988). Consequently, the individualization of the ECTemp™ model is a topic of interest for future research.

An example of a function for use in MatLab with annotations, which based on this disclosure it should be appreciated could be omitted, is as follows:

```
function CT=KFModel(heart rate,CTstart)
%Inputs:
%heart rate=A vector of minute to minute heart rate values.
%CTstart=Core Body Temperature at time 0.
%Outputs:
```

```
%core body temperature=A vector of minute to minute core body temperature estimates
%Extended Kalman Filter Parameters
a=1; gamma=0.0222;
b_0=-7887.1; b_1=384.4286; b_2=-4.5714; sigma=18.882;
%Initialize Kalman filter
x=CTstart; v=0;%v=0 assumes confidence with start value.
%Iterate through heart rate time sequence
for time=1:length(heart rate)
%Time Update Phase
x_pred=a*x; %Equation 3
v_pred=(a^2)*v+gamma; %Equation 4%
%Observation Update Phase
z=heart rate (time);
c_vc=2.*b_2.*x_pred+b_1; %Equation 5
k=(v_pred.*c_vc)./((c_vc.^2).*v_pred+sigma); %Equation 6
x=x_pred+k.*(z-(b_2.*(x_pred.^2)+b_1.*x_pred+b_0)); %Equation 7
v=(1-k.*c_vc).*v_pred; %Equation 8
CT(time)=x;
end
```

As will be appreciated by one skilled in the art based on this disclosure, aspects of the present invention may be embodied as a system, method or computer program product. Accordingly, aspects of the present invention may take the form of an entirely hardware embodiment, a processor operating with software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Computer program code for carrying out operations for aspects of the present invention may be written in any combination of one or more programming languages, including an object oriented programming language such as Java, Smalltalk, C++, C#, Transact-SQL, XML, or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute with the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 9:
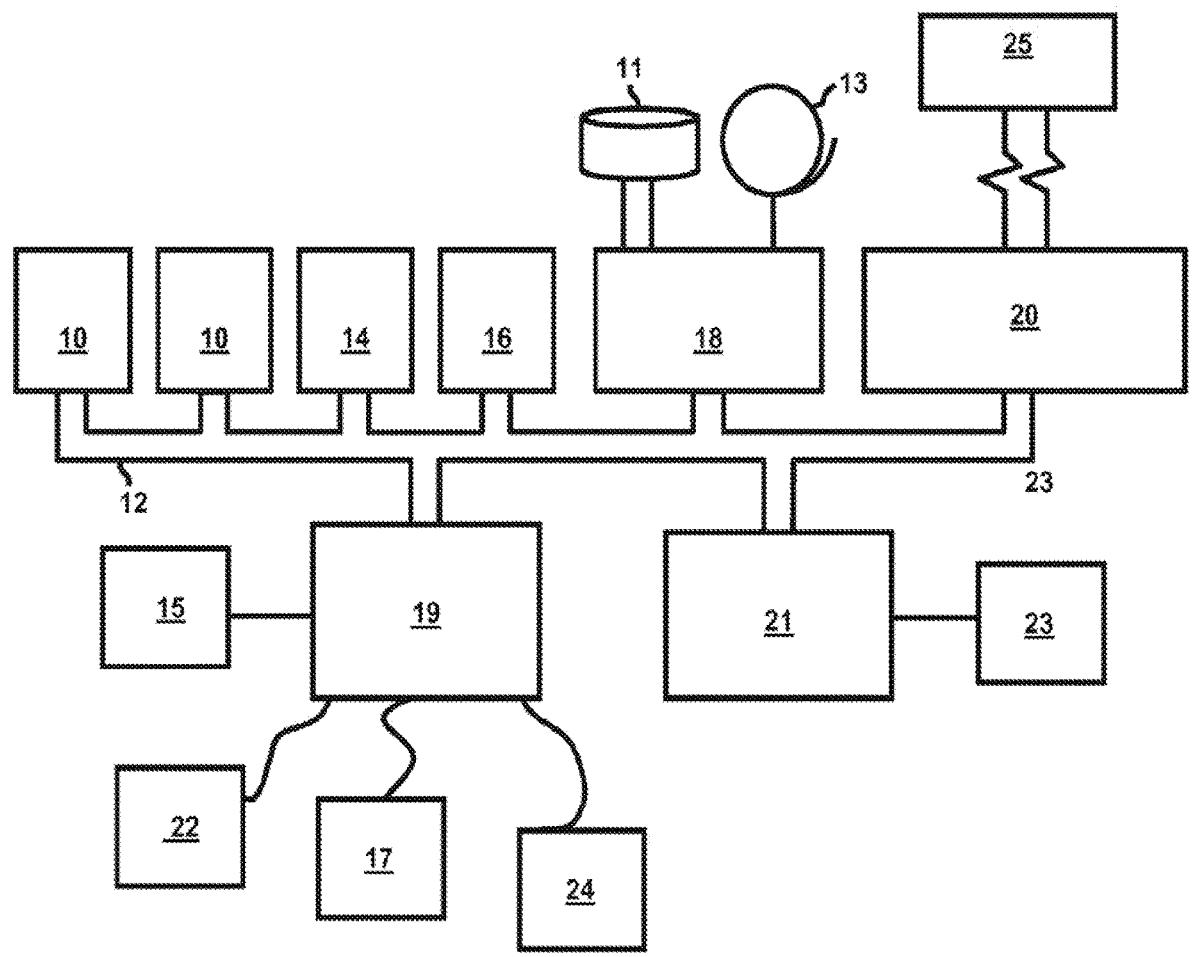
FIG. 9 illustrates a computer program product and computer implementation according to an embodiment of the invention.

Referring now to FIG. 9, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

Although the present invention has been described in terms of particular example embodiments, it is not limited to those embodiments. The embodiments, examples, and modifications which would still be encompassed by the invention may be made by those skilled in the art, particularly in light of the foregoing teachings.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

INDUSTRIAL APPLICABILITY

The information provided by the Kalman filter model can be used in at least one embodiment to determine whether a particular individual needs to take a break and/or seek treatment/assistance to cool down to lower their core body temperature.

REFERENCE LIST

The following articles have been referred to in this disclosure:

Al-Muhaizeem F, Allen U, Komar L, Naser B, Roy L, Stephens D, Read S, Kim C, Schuh S (2004), "Comparison of temporal artery, rectal and esophageal core temperature in children: results of a pilot study", *Pediatr. Child Health* 9(7):461-465.

Bland J M and Altman D G (1986), "Statistical methods for assessing agreement between two methods of clinical measurements", *The Lancet* 1(8476):307-310.

Buller M J, Tharion W J, Hoyt R W, Jenkins O C (2010), "Estimation of human internal temperature from wearable physiological sensors", *22nd Conference on Innovative Applications of Artificial Intelligence* (IAAI), 1763-1768.

Buller M J, Welles A P, Stower J, Desantis C, Margolis L, Karis A J, Economos D, Hoyt R W, Richter M W (2011), "*Thermal work strain during Marine rifle squad operations in Afghanistan* (March 2010)", USARIEM Technical Report No.: T11-02 (AD A501301).

Buller M J, Castellani J, Roberts W S, Hoyt R W, Jenkins O C (2011), "Human thermoregulatory system state estimation using non-invasive physiological sensors", *Conf. Proc. IEEE Eng. Med. Biol. Soc.* 3290-3293.

Buller, M J, Tharion, W J, Cheuvront, S N, Montain, S J, Kenefick, R W, Castellani, J, . . . Hoyt, R W (2013), "Estimation of human core temperature from sequential heart rate observations", *Physiological Measurement*, 34(7), 781-798.

Buller, M J, Tharion, W J, Duhamel, C M, & Yokota, M (2015), "Real-time core body temperature estimation from heart rate for first responders wearing different levels of personal protective equipment", *Ergonomics*, 58(11), 1830-1841.

Byrne C, Lim C L (2007), "The ingestible telemetric body core temperature sensor: a review of validity and exercise applications", *Br. J. Sports Med.* 41:126-133.

Consolazio C F, Johnson R E and Pecora L J (1963), "Physiological variability in young men" in *Physiological measurements of metabolic functions* (Eds) Consolazio C F, Johnson R E, Pecora L J McGraw Hill, New York, N.Y., pp 453-480.

Cheuvront S N, Montain S J, Goodman D A, Blanchard L, Sawka M N (2007), "Evaluation of the limits to accurate sweat loss prediction during prolonged exercise", *Eur. J. Appl. Physiol.* 101(2): 215-224.

DeGroot D W, Goodman D A, Montain S J, Cheuvront, S N (2008), "Validation of the ICDA Model for Predicting Body Core Temperature", *Medicine & Science in Sports & Exercise.* 40 (5): S367 (Abstract).

Fiala D, Lomas K J, Stohrer M (2001), "Computer prediction of human thermoregulatory and temperature responses to a wide range of environmental conditions", *Int. J. Biometeorol.* 45:143-59.

Fick A (1855), "On liquid diffusion", The London, Edinburgh, and Dublin Philosophical Magazine and *Journal of Science.* 10—Fourth Series (July-September), 30-39, 1855.

Frank A, Belokopytov M, Shapiro Y, Epstein Y (2001), "The cumulative heat strain index—a novel approach to assess the physiological strain induced by exercise heat stress", *Eur. J. Appl. Physiol.* 84: 527-532.

Fox R H, Solman A J, Isaacs R, Fry A J and MacDonald I C (1973), "A new method for monitoring deep body temperature from the skin surface", *Clin. Sci.* 44:81-6.

Grubbs, F E (1969), "Procedures for Detecting Outlying Observations in Samples", *Technometrics* 11(1):1-21.

Gunga H C, Sandsund M, Reinertsen R E, Sattler F, Koch J (2008), "A non-invasive device to continuously determine heat strain in humans", *J. Thermal Biology* 33:297-307.

Gunga H C, Werner A, Stahn A, Steinach M, Schlabs T, Koralewski E, Kunz D, Belavy' D L, Felsenberg D, Sattler F, Koch J (2009), "The Double Sensor—A non-invasive device to continuously monitor core temperature in humans on earth and in space. *Respiratory Physiology & Neurobiology",* 169S:S63-S68.

Havenith G (2001), "Individualized model of human thermoregulation for the simulation of heat stress response", *J. Appl. Physiol.* 90:1943-1954.

Jagannath, A, Peirson, S N, & Foster, R G (2013), "Sleep and circadian rhythm disruption in neuropsychiatric illness", *Current Opinion in Neurology,* 23(5), 888-894.

Kenefick R W, Cheuvront S N, Ely B R, Palombo L J, Sawka M N (2011), "DEET insect repellent: effects on thermoregulatory sweating and physiological strain", *Eur. J. Appl. Physiol.* 111(12):3061-3068.

Kraning K K, Gonzalez R R (1997), "A mechanistic computer simulation of human work in heat that accounts for physical and physiological effects of clothing, aerobic fitness, and progressive dehydration", *J. Therm. Biol.* 22 (4/5): 331-342.

Latzka W A, Sawka M N, Montain S J, Skrinar G S, Fielding R A, Matott R P, Pandolf K B (1997), "Hyperhydration: thermoregulatory effects during compensable exercise-heat stress", *J. Appl. Physiol.* 83(3): 860-866.

Latzka W A, Sawka M N, Montain S J, Skrinar G S, Fielding R A, Matott R P, Pandolf K B (1998), "Hyperhydration: tolerance and cardiovascular effects during uncompensible exercise-heat stress", *J. Appl. Physiol.* 84: 1858-1864.

Lee J K, Nio A Q Lim C L, Teo E Y, Byrne C (2010), "Thermoregulation, pacing and fluid balance during mass participation distance running in a warm humid environment", *Eur. J. Appl. Physiol.* 107(5):1519-25.

Lefrant J Y, Muller L, Coussaye J E, Benbabaali M, Lebris C, Zeitoun N, Mari C, Saissi G, Ripart J, Eledjam J J (2003), "Temperature measurement in intensive care patients: comparison of urinary bladder, oesophageal, rectal, axillary, and inguinal methods versus pulmonary artery core method", *Intensive Care Med.* 29:414-418.

Lim C L, Byrne C, Lee J K W (2008), "Human thermoregulation and measurement of body temperature in exercise and clinical settings", *Annals Academy of Medicine* 37:347-353.

Looney, D P, Buller, M J, Welles, A P, Leger, J L, Stevens, M, Gribok, A, . . . Hoyt, R W (2017), "Accuracy of the estimated core temperature (ECTemp) algorithm in estimating circadian rhythm indicators" (Report No. T17-08, AD1031877), Natick, MA: US Army Research Institute of Environmental Medicine.

Looney at al. (Looney, D P, Buller, M J, Gribok, A V, Leger, J L, Potter, A W, Rumpler, W V, Tharion, W J, Welles, A P, Friedl, K E, & Hoyt, R W) (2018), "Estimating Resting Core Temperature Using Heart Rate", *J. for the Measurement of Physical Behaviour,* 1, 79-86.

Montain S J, Coyle E F (1992), "Influence of graded dehydration on hyperthermia and cardiovascular drift during exercise", *J. Appl. Physiol.* 73(4): 1340-1350.

Moran D S, Shitzer A and Pandolf K B (1998), "A physiological strain index to evaluate heat stress", *Am. J. Physiol. Regulatory Integrative Comp. Physiol.* 275: 129-134.

Niedermann, R, Wyss, E, Annaheim, S, Psikuta, A, Davey, S, & Rossi, R M (2014), "Prediction of human core body temperature using non-invasive measurement methods", *Int'l J. of Biometeorology,* 58(1), 7-15.

Potter, A W, Blanchard, L A, Friedl, K E, Cadarette, B S, & Hoyt, R W (2017), "Mathematical prediction of core body temperature from environment, activity, and clothing: The heat strain decision aid (HSDA)", *J. of Thermal Biology,* 64, 78-85.

Refinetti, R, Lissen, G C, & Halberg, F (2007), "Procedures for numerical analysis of circadian rhythms", *Biological Rhythm Research,* 38(4), 275-325.

Richards, F (1959), "A flexible growth function for empirical use", *J. of Experimental Botany,* 10(2), 290-301.

Richmond, V L, Davey, S, Griggs, K, & Havenith, G (2015), "Prediction of core body temperature from multiple variables", *Annals of Occupational Hygiene,* 59(9), 1168-1178.

Savvidis, C & Koutsilieris, M (2012), "Circadian rhythm disruption in cancer biology", *Molecular Medicine,* 18, 1249-1260.

Sawka M N, Young A J (2006), "Physiological systems and their responses to conditions of heat and cold" in *ACSM's Advanced Exercise Physiology,* (eds) Tipton C M, Sawka M N, Tate C A, Terjung R L., American College of Sports Medicine, Lipcot, Williams & Wilkins. New York, N.Y. pp 535-563.

Shi, S Q Ansari, T S, McGuinness, O P, Wasserman, D H, & Johnson, C H (2013), "Circadian disruption leads to insulin resistance and obesity", *Current Biology*, 23(5), 372-381.

Sim, S Y, Joo, K M, Kim, H B, Jang, S J, Kim, B O, Hong, S B, Park, K S (2016), "Estimation of circadian body temperature rhythm based on heart rate in healthy, ambulatory subjects", *IEEE J. of Biomedical and Health Informatics*, 21(2), 407-415.

Steck L N, Sparrow E M, Abraham J P (2011), "Non-invasive measurement of the human core temperature", International *Journal of Heat and Mass Transfer* 54:975-982.

Teunissen L P J, Klewer J, de Haan A, de Konig J J, and Daanen H A M (2011), "Non-invasive continuous core temperature measurement by zero heat flux", *Physiological Measurement* 32:559-570.

Tharion, W J, Buller, M J, Potter, A W, Karis, A J, Goetz, V, & Hoyt, R W (2013), "Acceptability and usability of an ambulatory health monitoring system for use by military personnel", *IIE Transactions on Occupational Ergonomics and Human Factors*, 1, 203-214.

Welch, G & Bishop, G (1995), "An introduction to the kalman filter (TR 95-041)", Chapel Hill, NC: U. of N.C.

Welles, A P, Buller, M J, Looney, D P, Rumpler, W V, Gribok, A V, & Hoyt, R W (2018), "Estimation of metabolic energy expenditure from core temperature using a human thermoregulatory model", *J. of Thermal Biology*, 72, 44-52.

Wilkinson D M, Carter J M, Richmond V L, Blacker S D and Rayson M P (2008), "The effect of cool water ingestion on gastrointestinal pill temperature", *Med. Sci. Sports Exerc.* 40(3): 523-528.

Yamakage M, Iwasaki S, Namiki A (2002), "Evaluation of newly developed monitor of deep body temperature", *J. Anesth.* 16:354-357.

Yokota M, Berglund L, Cheuvront S, Santee W, Latzka W, Montain S, Kolk M, Moran D (2008), "Thermoregulatory model to predict physiological status from ambient environment and heart rate", *Computers in Biology and Medicine* 38: 1187-1193.

The invention claimed is:

1. A method for indirectly predicting a core body temperature of a person in substantially real-time to allow the person to act on the core body temperature to avoid a heat illness, the method comprising:
   setting an initial core body temperature with a mobile device comprising a heart rate monitor, a processor, and a display;
   receiving at least two heart rates of the person with the processor, where the heart rates are detected by the heart rate monitor attached to the person, wherein the at least two heart rates include a first heart rate and a second heart rate;
   calculating the core body temperature with the processor using an extended Kalman filter based on a sigmoid model using solely the second heart rate and the initial core body temperature;
   providing the core body temperature to the display and/or an external device; and,
   using the provided core body temperature by the person to adjust an activity level in real-time when the core body temperature indicates there is an elevated risk of suffering from heat illness, and
   wherein the initial core body temperature is set by the processor
      based solely on the first heart rate of the person or
      on a predetermined resting core body temperature for that person; and
   the sigmoid model uses an error between the measured heart rate and an estimated heart rate based on the estimated core body temperature to adjust the sigmoid model.

2. The method according to claim 1, further comprising:
   receiving an additional heart rate of the person with the processor, where the additional heart rate is detected by the heart rate monitor;
   calculating a new predicted core body temperature with the processor using the extended Kalman filter based on the sigmoid model using solely the additional heart rate and the last predicted core body temperature from the last calculation of the core body temperature; and
   repeating the receiving additional heart rate and calculating a new predicted core body temperature at predetermined intervals.

3. The method according to claim 2, further comprising:
   when the new predicted core body temperature exceeds a predetermined threshold, sending an alarm signal from said processor prior to proceeding to repeating, wherein the alarm signal triggers an alarm; and
   when the new predicted core body temperature does not exceed a predetermined threshold, proceeding to repeating.

4. The method according to claim 2, wherein the method repeats on predetermined intervals of 1 minute intervals, 2 minute intervals, or 5 minute intervals.

5. The method according to claim 1, further comprising recording the predicted core body temperature in memory in the mobile device; and
   wherein the extended Kalman filter includes a time update model and an observation update model.

6. The method according to claim 1, wherein providing the predicted core body temperature includes transmitting the predicted core body temperature with a transmitter in the mobile device to an external device.

7. The method according to claim 1, wherein calculating the predicted core body temperature includes
   computing a preliminary core body temperature estimate;
   computing a preliminary estimate of the variance of the preliminary core body temperature estimate;
   computing an extended Kalman filter mapping function variance coefficient;
   computing a Kalman gain weighting factor based on the preliminary estimate of variance and the extended Kalman filter mapping function variance coefficient; and
   computing the predicted core body temperature ($CT_t$) using a preliminary core body temperature estimate ($\hat{CT}_t$), and an error between the new heart rate ($HR_t$) and an expected heart rate given the preliminary estimate of the core body temperature with the following relationship $$CT_t = \hat{CT}_t + k_t \left\{ HR_t - \left( 41 + \frac{152}{\left(1 + 0.06 e^{-089(\hat{CT}_t - 37.84)}\right)^{1/0.07}} \right) \right\},$$

and
wherein the expected heart rate (expected HR) is determined based on $$\text{expected } HR_t = A + \frac{K-A}{\left(1 + Qe^{-B(\hat{C}T_t - M)}\right)^{1/v}}$$

where A=lower asymptote, K=upper asymptote, Q=is the value when estimated core temperature ($\hat{C}T_t$)=M, B=the growth rate, M=sets the starting $\hat{C}T_t$ value, and v=affects the asymptote where maximum growth occurs, or
the expected heart rate (expected HR) is determined based on $$\text{expected } HR = 41 + \frac{152}{\left(1 + 0.06e^{-0.89(\hat{C}T_t - 37.84)}\right)^{1/0.07}}.$$

8. The method according to claim 1, wherein a relationship between the core body temperature and the heart rate is a sigmoid relationship that varies over a range of heart rate measurements.

9. The method according to claim 1, further comprising:
receiving from an accelerometer activity data;
determining based on the activity data whether the person is exercising or resting; and
changing the extended Kalman filter based on the activity data to affect a rate of core temperature rise or fall.

10. A mobile device for indirectly determining a core body temperature of a person to allow the person to act on the core body temperature to avoid a heat illness, the mobile device comprising:
a heart rate monitor capable of attachment to the person whose core body temperature is being determined;
a memory to store core body temperature data;
a processor in communication with said heart rate monitor, said processor calculates a core body temperature using an extended Kalman filter having a plurality of constants and the extended Kalman filter is based on a sigmoid model having as the only inputs a heart rate from said heart rate monitor and prior core body temperature data stored in said memory; and
a display in communication with said processor, and
wherein the sigmoid model uses an error between the measured heart rate and an estimated heart rate based on the estimated core body temperature to adjust the sigmoid model; and
wherein said processor provides the calculated core body temperature in real-time to said display, the person acts on the displayed calculated core body temperature by adjusting an activity level when the calculated core body temperature indicates the person is at an elevated risk of suffering from heat illness.

11. The mobile device according to claim 10, further comprising a transmitter for communication with an external system, said transmitter in communication with said processor.

12. The mobile device according to claim 10, wherein the processor is configured to calculate the core body temperature by
computing a preliminary core body temperature estimate;
computing a preliminary estimate of the variance of the preliminary core body temperature estimate;
computing an extended Kalman filter mapping function variance coefficient;
computing a Kalman gain weighting factor based on the preliminary estimate of variance and the extended Kalman filter mapping function variance coefficient; and
computing the predicted core body temperature ($CT_t$) using a preliminary core body temperature estimate ($\hat{C}T_t$), and an error between the new heart rate ($HR_t$) and an expected heart rate given the preliminary estimate of the core body temperature with the following relationship $$CT_t = \hat{C}T_t + k_t\left\{HR_t - \left(41 + \frac{152}{\left(1 + 0.06e^{-0.89(\hat{C}T_t - 37.84)}\right)^{1/0.07}}\right)\right\},$$

and
wherein the expected heart rate (expected HR) is determined based on $$\text{expected } HR_t = A + \frac{K-A}{\left(1 + Qe^{-B(\hat{C}T_t - M)}\right)^{1/v}}$$

where A=lower asymptote, K=upper asymptote, Q=is the value when estimated core temperature ($\hat{C}T_t$)=M, B=the growth rate, M=sets the starting $\hat{C}T_t$ value, and v=affects the asymptote where maximum growth occurs.

13. The mobile device according to claim 10, wherein said processor includes
an initial core body temperature module for setting an initial core body temperature,
a heart rate module for obtaining the heart rate based on a signal from said heart rate monitor, and
a core body temperature calculator module for calculating the core body temperature, said core body temperature calculator module in communication with said initial core body temperature module and said heart rate module.

14. The mobile device according to claim 13, where said processor further includes a timer module in communication with said heart rate module and said core body temperature calculator module.

15. The mobile device according to claim 14, where said processor further includes an alarm module for triggering an alarm when the core body temperature exceeds a threshold, said alarm module in communication with said core body temperature calculator module.

16. The mobile device according to claim 15, further comprising:
a display in communication with said core body temperature calculator module;
a transmitter in communication with said core body temperature calculator module; and
a temperature sensor in communication with at least one of said timer module and said alarm module.

17. The mobile device according to claim 10, wherein a relationship between the core body temperature and the heart rate is a sigmoid relationship that varies over a range of heart rate measurements.

18. A mobile device for indirectly determining a core body temperature of a person based on a heart rate to allow the person to act on the core body temperature to avoid a heat illness, the mobile device comprising:
- a heart rate monitor attached to a heart rate monitor processor configured to convert signals from said heart rate monitor into the heart rate, said heart rate monitor configured to contact the person during use; and
- a processor in communication with said heart rate monitor, said processor having program code embodied therewith, the program code executable by the processor in real time to
  - set an initial core body temperature;
  - receive the heart rate of the person from said heart rate monitor;
  - calculate the core body temperature using an extended Kalman filter based on a sigmoid model having as its only inputs the heart rate and at least one of the initial core body temperature and the prior core body temperature; and
  - provide the core body temperature of the person, and
  - wherein the person reduces the activity level in response to the provided core body temperature when the core body temperature indicates an elevated risk of suffering from heat illness,
  - wherein the sigmoid model uses an error between the measured heart rate and an estimated heart rate based on the estimated core body temperature to adjust the sigmoid model.

19. The mobile device according to claim 18, further comprising:
- a display in communication with said processor; and
- a transmitter in communication with said processor, and
- wherein the initial core body temperature is set based on the initial heart rate of the person.

20. The mobile device according to claim 18, wherein said processor having further program code embodied therewith, the further program code executable by the processor to calculate the predicted core body temperature by

- computing a preliminary core body temperature estimate;
- computing a preliminary estimate of the variance of the preliminary core body temperature estimate;
- computing an extended Kalman filter mapping function variance coefficient;
- computing a Kalman gain weighting factor based on the preliminary estimate of variance and the extended Kalman filter mapping function variance coefficient; and
- computing the predicted core body temperature (CT) using a preliminary core body temperature estimate ($\hat{C}T_t$), an error between the new heart rate ($HR_t$) and an expected heart rate given the preliminary estimate of the core body temperature with the following relationship $$CT_t = \hat{C}T_t + k_t\left\{HR_t - \left(41 + \frac{152}{\left(1 + 0.06e^{-0.89(\hat{C}T_t - 37.84)}\right)^{1/0.07}}\right)\right\},$$

and wherein the expected heart rate (expected HR) is determined based on $$\text{expected } HR_t = A + \frac{K - A}{\left(1 + Qe^{-B(\hat{C}T_t - M)}\right)^{1/\nu}}$$

where A=lower asymptote, K=upper asymptote, Q=is the value when estimated core temperature ($\hat{C}T_t$)=M, B=the growth rate, M=sets the starting $\hat{C}T_t$ value, and ν=affects the asymptote where maximum growth occurs.

* * * * *